United States Patent
Richards

(10) Patent No.: US 10,441,621 B2
(45) Date of Patent: Oct. 15, 2019

(54) FLAVONOID COMPOSITIONS AND METHODS OF USE

(71) Applicant: Reoxcyn, LLC, Pleasant Grove, UT (US)

(72) Inventor: Kurt Richards, Herriman, UT (US)

(73) Assignee: REOXCYN, LLC, Pleasant Grove, UT (US)

( * ) Notice: Subject to any disclaimer, the term of this patent is extended or adjusted under 35 U.S.C. 154(b) by 215 days.

(21) Appl. No.: 15/396,201

(22) Filed: Dec. 30, 2016

(65) Prior Publication Data

US 2017/0106036 A1 Apr. 20, 2017

Related U.S. Application Data

(63) Continuation-in-part of application No. 15/272,826, filed on Sep. 22, 2016, now Pat. No. 9,839,624.

(60) Provisional application No. 62/222,667, filed on Sep. 23, 2015.

(51) Int. Cl.
| | |
|---|---|
| *A61K 36/82* | (2006.01) |
| *A61K 9/00* | (2006.01) |
| *A61K 31/352* | (2006.01) |
| *A61K 36/45* | (2006.01) |
| *A61K 31/341* | (2006.01) |
| *A61K 31/522* | (2006.01) |
| *A61K 31/202* | (2006.01) |
| *A61K 31/353* | (2006.01) |

(52) U.S. Cl.
CPC ............ *A61K 36/82* (2013.01); *A61K 9/0056* (2013.01); *A61K 31/202* (2013.01); *A61K 31/341* (2013.01); *A61K 31/352* (2013.01); *A61K 31/353* (2013.01); *A61K 31/522* (2013.01); *A61K 36/45* (2013.01)

(58) Field of Classification Search
None
See application file for complete search history.

(56) References Cited

U.S. PATENT DOCUMENTS

| | | |
|---|---|---|
| 6,821,536 B2 | 11/2004 | Lines et al. |
| 8,318,224 B2 | 11/2012 | Lines et al. |
| 8,747,915 B1 | 6/2014 | Giampapa |
| 8,846,061 B1 | 9/2014 | Bezzek |
| 2005/0266121 A1 | 12/2005 | Lines |
| 2006/0172012 A1 | 8/2006 | Finley et al. |
| 2009/0018186 A1 | 1/2009 | Chen et al. |
| 2014/0322389 A1 | 10/2014 | Prakash et al. |
| 2015/0023941 A1 | 1/2015 | Bagley |

FOREIGN PATENT DOCUMENTS

| | | |
|---|---|---|
| CN | 101632655 | 1/2010 |
| RU | 2387136 C2 | 4/2010 |

OTHER PUBLICATIONS

First Examination Report in NZ application No. 741022, dated Jul. 11, 2018.
Office Action issued in related AU application No. 2016326523, dated Nov. 20, 2018.
Alm et al.: "Effects of topically applied PGF2 alpha and its isopropylester on normal and glaucomatous human eyes," Prog. Clin. Biol. Res., 312:447-58 (1989).
Bakker et al.: "An antiinflammatory dietary mix modulates inflammation and oxidative and metabolic stress in overweight men: a nutrigenomics approach," Am. J. Clin. Nutr., 91:1044-59 (2010).
Chun et al.: "Estimation of antioxidant intakes from diet and supplements in U.S. adults," J. Nutr., 140:317-24 (2010).
Hooper et al.: "Flavonoids, flavonoid-rich foods, and cardiovascular risk: a meta-analysis of randomized controlled trials," Am. J. Clin. Nutr., 88:38-50 (2008).
International search Report and Written Opinion for PCT/US2016/053141 dated Dec. 6, 2016.
Joshi: "Microparticulates for ophthalmic drug delivery," J. Ocul. Pharmacol., 10(1):29-45 (1994).
Kale et al.: "Studies on the effects of oral administration of nutrient mixture, quercetin and red onions on the bioavailability of epigallocatechin gallate from green tea extract," Phytother Res., 24 (Suppl 1):S48-55 (2010).
Lila: "From beans to berries and beyond: teamwork between plant chemicals for protection of optimal human health," Ann. N Y Acad. Sci., 1114:372-80 (2007).
Mayer et al.: "Efficacy of a novel hydrogel formulation in human volunteers," Ophthalmologica, 210(2):101-3 (1996).
Mordenti: "Intraocular pharmacokinetics and safety of a humanized monoclonal antibody in rabbits after intravitreal administration of a solution or a PLGA microsphere formulation," Toxicol. Sci., 52(1):101-6 (1999).
Shanely et al.: "Quercetin supplementation does not alter antioxidant status in humans," Free Radic. Res., 44:224-31 (2010).
Shedden et al.: "Efficacy and tolerability of timolol maleate ophthalmic gel-forming solution versus timolol ophthalmic solution in adults with open-angle glaucoma or ocular hypertension: a six-month, double-masked, multicenter study," Clin. Ther., 23(3):440-50 (2001).
Terao et al.: "Vegetable flavonoids and cardiovascular disease," Asia Pac. J. Clin. Nutr., 17(Suppl 1): 291-3 (2008).
USDA Nutrient Data Laboratory. USDA Database for the Flavonoid Content of Selected Foods, Beltsville, Md.: U.S. Dept. of Agriculture (2007).

(Continued)

*Primary Examiner* — Susan Hoffman
(74) *Attorney, Agent, or Firm* — Knobbe, Martens Olson & Bear LLP

(57) ABSTRACT

Flavonoid compositions containing the flavonoid quercetin and/or derivatives of quercetin are disclosed. The flavonoid compositions are formulated to improve the bioavailability of quercetin. Also provided herein are methods for improving athletic performance, improving cardiovascular health, and aiding in immune response and methods of improving athletic performance, improving bone health, preventing fatigue, reducing recovery time after exercise, countering oxidative stress, and/or boosting energy.

19 Claims, 15 Drawing Sheets

(56) References Cited

OTHER PUBLICATIONS

Wang et al.: "Dietary intake of selected flavonols, flavones, and flavonoid-rich foods and risk of cancer in middle-aged and older women," Am. J. Clin. Nutr. 89:905-12 (2009).
Zamora-Ros et al.: "Estimation of dietary sources and flavonoid intake in a Spanish adult population (EPIC-Spain)," J. Am. Diet Assoc., 110:390-8 (2010).
Zamora-Ros et al.: "High concentrations of a urinary biomarker of polyphenol intake are associated with decreased mortality in older adults," J. Nutr., 143:1445-50 (2013).
Zhang et al.: "Intestinal and hepatic glucuronidation of flavonoids," Mol. Pharm., 4:833-45 (2007).
Office Action issued in RU application No. 2018107713, dated Jan. 9, 2019.
Office Action issued in CA application No. 2999763, dated Jan. 24, 2019.
Jeong, Yun-Mi et al. Cytoprotective effect of green tea extract and quercetin against hydrogen peroxide-induced oxidative stress. 2005.
European Extended Search Report dated Mar. 1, 2019, in related European patent Application No. 16849605.7.

Quercetin

Quercetin 4'-glucoside

Quercetin 3,4'-diglucoside

FLAVONOID COMPOSITIONS AND METHODS OF USE

RELATED APPLICATIONS

This application is a continuation-in-part of U.S. patent application Ser. No. 15/272,826, filed Sep. 22, 2016, now U.S. Pat. No. 9,839,624 which claims the benefit of priority to U.S. Provisional Patent Application No. 62/222,667, filed Sep. 23, 2015, the disclosure of each of which is incorporated by reference herein in its entirety.

FIELD OF THE DISCLOSURE

This disclosure pertains to flavonoid compositions and methods of using such flavonoid compositions. More particularly, it pertains to flavonoid compositions that are formulated for use by human and/or animal subjects. The flavonoid compositions can include a flavonoid, for example, the flavonoid quercetin and/or derivatives of quercetin, in a form that can be easily administered to a human and/or animal subject. The flavonoid compositions can also be configured to increase the bioavailability, absorption, distribution, metabolism, and/or excretion of quercetin. The flavonoid compositions can also comprise other additives to increase the bioavailability, absorption, distribution, metabolism, and/or excretion of quercetin.

BACKGROUND

Phytochemicals are chemicals produced by plants, and include tannins, lignins, and flavonoids. The largest and best studied polyphenols are the flavonoids, with more than 8,000 identified and classified into at least six subgroups: flavonols, flavones, flavanones, flavanols (and their oligomers, proanthocyanidins), anthocyanidins, and isoflavonoids (Table 1) (USDA Nutrient Data Laboratory. USDA Database for the Flavonoid Content of Selected Foods. (2007) Beltsville, Md.: U.S. Dept. of Agriculture). Only about 100 polyphenols are in foods humans typically eat. Flavonoids are widely distributed in plants and function as plant pigments, signaling molecules, and defenders against infection and injury.

TABLE 1

Flavonoid Classification, Examples, and Sources

| Flavonoid Subgroup | Specific Flavonoids | Food Sources |
| --- | --- | --- |
| Flavonols | Quercetin, kaempferol, myricetin, isorhamnetin | onions, apples, leafy vegetables, berries |
| Flavones | Luteolin, apigenin | parsley, hot peppers, celery, artichokes, spices |
| Flavanones | Hesperetin, naringenin, eriodictyol | citrus fruits and citrus juices |
| Flavan-3-ols | Catechins, epigallocatechins, theaflavins | tea, chocolate, tree fruits, grape seed |
| Anthocyanidins | Cyaniding, delphinidin, malvidin, pelargonidin, peonidin, petunidin | most berries, cowpeas |
| Isoflavones | Daidzein, genistein, glycitein | soybeans, soyfoods |

Dietary intake of flavonoids ranges from 50 to 800 mg/day depending on the consumption of the food source containing various flavonoids. In the U.S., total flavonoid intake averages 251 mg/day (Chun O K, Floegel A, Chung S J, et al. Estimation of antioxidant intakes from diet and supplements in U.S. adults. J Nutr 2010; 140:317-24; the disclosure of which is incorporated by reference herein in its entirety), and in Spain 313 mg/day (Zamora-Ros R, Andres-Lacueva C, Lamuela-Raventós R M, et al. Estimation of dietary sources and flavonoid intake in a Spanish adult population (EPIC-Spain). J Am Diet Assoc 2010; 110:390-8; the disclosure of which is incorporated by reference herein in its entirety), with important sources including tea, citrus fruit and juice, beers and ales, wines, melon and berries, apples, onions, and bananas. Only about 29% of individuals consume tea on a given day, and without tea consumption, the flavonoid intake is closer to about 50 mg/day, reflecting the low intake of fruits and vegetables by U.S. adults. The typical American is a low consumer of fruit (0.53 cups/1000 calories) and vegetables (0.77 cups/1000 calories), well below the *Healthy People* 2020 goals of 0.90 cups/1000 calories for fruit and 1.14 cups/1000 calories for vegetables.

A high intake of fruits and vegetables has been linked in numerous studies to reduced risk of cardiovascular disease and various types of cancer. The disease-reducing influence of fruits and vegetables may be due in part to high levels of flavonoids (Hooper L, Kroon P A, Rimm E B, et al. Flavonoids, flavonoid-rich foods, and cardiovascular risk: a meta-analysis of randomized controlled trials. Am J Clin Nutr 2008; 88:38-50; Wang L, Lee I M, Zhang S M, et al. Dietary intake of selected flavonols, flavones, and flavonoid-rich foods and risk of cancer in middle-aged and older women. Am J Clin Nutr 2009; 89:905-12; Zamora-Ros R1, Rabassa M, Cherubini A, Urpí-Sardà M, Bandinelli S, Ferrucci L, Andres-Lacueva C. High concentrations of a urinary biomarker of polyphenol intake are associated with decreased mortality in older adults. J Nutr. 2013; 143:1445-50). A 12-year study of 807 elderly men and women in Italy showed that those in the upper tertile for total urinary polyphenol concentration (a proxy measure of fruit and vegetable intake) experienced a 30% reduction in all-cause mortality (Zamora-Ros R1, Rabassa M, Cherubini A, Urpí-Sardà M, Bandinelli S, Ferrucci L, Andres-Lacueva C. High concentrations of a urinary biomarker of polyphenol intake are associated with decreased mortality in older adults. J Nutr. 2013; 143:1445-50). These data strongly support that a high polyphenol intake is associated with extended longevity.

Many flavonoids possess strong anti-inflammatory, antiviral, antioxidant, anti-obesity, and anti-carcinogenic properties when studied in vitro using large doses of the purified form. Inflammation and oxidative stress are key mechanisms in the pathogenesis of certain disease states, supporting the proposed strategy of increased flavonoid intake for prevention of cancer, diabetes mellitus, and cardiovascular disease. However, results from randomized, double-blinded studies in humans with large doses of purified flavonoids such as quercetin have been disappointing (Shanely R A, Knab A M, Nieman D C, et al. Quercetin supplementation does not alter antioxidant status in humans. Free Radic Res 2010; 44:224-31). Flavonoids vary widely in bioavailability, and most are poorly absorbed, undergo active efflux, and are extensively conjugated and metabolically transformed, all of which can affect their bioactive capacities (Zhang L, Zuo Z, Lin G. Intestinal and hepatic glucuronidation of flavonoids. Mol Pharm 2007; 4:833-45). Despite low bioavailability of the parent flavonoid, some of the in vivo metabolites may accumulate in tissues and produce bioactive influences, but conclusive human data are lacking. For example, animal data indicate that quercetin metabolites accumulate in the vascular tissue and there act as complementary antioxidants, with plasma albumin facilitating the translocation of quercetin metabolites to the vascular target (Terao J, Kawai Y, Murota K. Vegetable flavonoids and cardiovascular disease. Asia Pac J Clin Nutr 2008; 17(Suppl 1): 291-3).

There is a growing realization that bioactive influences of individual flavonoids are potentiated when mixed with other flavonoids (for example, the flavonol quercetin with the flavanol epigallocatechin 3-gallate (EGCG)) or included in a cocktail or extract of other polyphenols and nutrients (Lila M A. From beans to berries and beyond: teamwork between plant chemicals for protection of optimal human health. Ann N Y Acad Sci 2007; 1114:372-80). Two or more flavonoids ingested together may increase bioavailability and decrease elimination via competitive inhibition of glucuronide and sulfate conjugation in both the intestine and liver, and by inhibiting efflux transporters such as P-glycoprotein, breast cancer resistance protein (BCRP), and multidrug resistance protein 2 (MRP2) (Kale A, Gawande S, Kotwal S, et al. Studies on the effects of oral administration of nutrient mixture, quercetin and red onions on the bioavailability of epigallocatechin gallate from green tea extract. Phytother Res 2010; 24 (Suppl 1):S48-55).

The health-protective effects of plant foods are not produced by a single component but rather complex mixtures of interacting molecules (Lila M A. From beans to berries and beyond: teamwork between plant chemicals for protection of optimal human health. Ann N Y Acad Sci 2007; 1114:372-80). The polyphenols and natural components provide a multifaceted defensive strategy for both plants and humans. Thus the "pharma" approach of using large doses of a single bioactive molecule is seldom successful in the application of nutrition to human health and performance. Additionally, a metabolomics or nutrigenomics approach is needed to improve the capacity of investigators to capture the complex and subtle influences of flavonoid supplements or flavonoid-rich extracts, foods, and beverages on whole-body metabolism and physiology (Bakker G C, van Erk M J, Pellis L, et al. An antiinflammatory dietary mix modulates inflammation and oxidative and metabolic stress in overweight men: a nutrigenomics approach. Am J Clin Nutr 2010; 91:1044-59).

Quercetin is a flavonol compound that is found in many fruits and vegetables, such as red onions, capers, black plums, blueberries, and red applies. It has been reported to provide numerous health benefits to humans that ingest the compound. These reported health benefits include acting as a powerful antioxidant, improving athletic performance, improving cardiovascular health, and aiding in immune response. Some studies have found that quercetin can reduce blood pressure and LDL cholesterol. Other studies have found that quercetin can increase athletic performance.

Although quercetin can provide numerous benefits, many people may not be able to fully realize its benefits. For example, for many people there may not be a convenient source of quercetin available to them. In some cases, some people may not enjoy the taste and/or flavors of natural sources of quercetin. In other instances, some people may not be able to consume sufficient amounts of quercetin to receive a beneficial effect. In other cases, some people may not be able to consume quercetin in a manner that makes the quercetin bioavailable.

Therefore, challenges currently exist in realizing the benefits of quercetin. Accordingly, it would be an improvement in the art to provide compositions and methods to more fully realize the benefits of quercetin.

SUMMARY

Flavonoid compositions and methods of use are disclosed herein. In some embodiments, the flavonoid composition can include a flavonoid in combination with one or more of an antioxidant, an anthocyanidin, a stimulant, a lipid, ascorbic acid, an omega-3 fatty acid, and ascorbyl palmitate.

In some embodiments, the flavonoid includes quercetin or a derivative or analogue thereof. In some embodiments, the flavonoid includes quercetin, aglycone quercetin, quercetin glycoside, isoquercetin, or combinations thereof. In some embodiments, the antioxidant is green tea extract or epicatechin or a derivative thereof. In some embodiments, the antioxidant is epigallocatechin gallate (EGCG). In some embodiments, the anthocyanidin is a blueberry anthocyanidin. In some embodiments, the stimulant is caffeine. In some embodiments, the lipid is n3 polyunsaturated fatty acid (N3-PUFA). In some embodiments, ascorbic acid is vitamin C. In some embodiments, the omega-3 fatty acid is an omega 3 powder, which can include, for example eicosapentaenoic acid or docosahexaenoic acid.

In some embodiments, the flavonoid composition can include about 10-500 mg of flavonoid. In some embodiments, the flavonoid composition includes about 52 mg of flavonoid. In some embodiments, the flavonoid composition includes about 10-500 mg of antioxidant. In some embodiments, the flavonoid composition includes about 90 mg EGCG. In some embodiments, the flavonoid composition includes about 10-500 mg of anthocyanidin. In some embodiments, the flavonoid composition includes about 225 mg anthocyanidin. In some embodiments, the flavonoid composition includes about 10-500 mg of stimulant. In some embodiments, the flavonoid composition includes about 52 mg of stimulant. In some embodiments, the flavonoid composition includes about 10-500 mg of lipid. In some embodiments, the flavonoid composition includes about 100 mg of lipid. In some embodiments, the flavonoid composition includes about 10-500 mg of ascorbic acid. In some embodiments, the flavonoid composition includes about 100 mg of ascorbic acid. In some embodiments, the flavonoid composition includes about 10-500 mg of omega-3 fatty acid. In some embodiments, the flavonoid composition includes about 100 mg of omega-3 fatty acid. In some embodiments, the flavonoid composition includes about 10-500 mg of ascorbyl palmitate. In some embodiments, the flavonoid composition includes about 60 mg of ascorbyl palmitate.

In some embodiments the flavonoid composition can include about 34% (w/w) wild fresh blueberry extract, about 8% (w/w) caffeine, about 12% (w/w) vitamin C, about 14% (w/w) green tea extract, about 15% (w/w) omega-3 powder, about 8% (w/w) quercetin, and about 9% (w/w) ascorbyl palmitate. In other embodiments, the flavonoid composition includes an additive configured to increase bioavailability of quercetin. In yet other embodiments, the flavonoid composition is administered to human subjects to improve athletic performance.

In some embodiments is provided a flavonoid composition including quercetin or an analogue or derivative thereof. In some embodiments, the analogue or derivative of quercetin is aglycone quercetin, quercetin glycoside, isoquercetin, or combinations thereof. In some embodiments, the flavonoid composition further includes one or more of green tea extract, blueberry anthocyanidins, caffeine, N3-PUFA, vitamin C, omega-3 powder, and ascorbyl palmitate.

In some embodiments, the composition is formulated as a chewable tablet, a chewable wafer, a capsule, a swallowable tablet, a stick pack, a powder sachet, gummi chews, tub and scoop, or other formulation.

Accordingly, in some embodiments is a flavonoid composition, including quercetin. In some embodiments, quercetin is aglycone quercetin, quercetin glycoside, or isoquercetin. In some embodiments, the flavonoid composition includes green tea extract, blueberry anthocyanidins, caffeine, or N3-PUFA.

In some embodiments is provided a flavonoid composition, including 33.9% (w/w) blueberry extract; 7.9% (w/w) caffeine; 12.6% (w/w) vitamin C; 13.6% (w/w) green tea extract; 15.1% (w/w) omega-3; 7.9% (w/w) quercetin; and 9.0% ascorbyl palmitate.

In some embodiments is provided an oral ingestible medicament, including quercetin or an analogue or derivative thereof, epigallocatechin 3-gallate (EGCG), blueberry anthocyanidins, caffeine, n-3 polyunsaturated fatty acids (PUFA), and vitamin C.

In some embodiments, quercetin or an analogue or derivative thereof is present in an amount ranging from about 10-500 mg. In some embodiments, quercetin or an analogue or derivative thereof is present in an amount of about 100 mg. In some embodiments, quercetin or an analogue or derivative thereof is present in an amount of about 52 mg.

In some embodiments, quercetin or an analogue or derivative thereof is present in an amount of about 100 mg, EGCG is present in an amount of about 90-180 mg, blueberry anthocyanidins is present in an amount of about 120-240 mg, caffeine in present in an amount of about 100 mg, N3-PUFA is present in an amount of about 100 mg, and vitamin C is present in an amount of about 100 mg. In some embodiments, the composition or medicament includes ascorbyl palmitate.

In some embodiments, quercetin or an analogue or derivative thereof is present in an amount of about 52 mg, EGCG is present in an amount of about 90 mg, blueberry anthocyanidins is present in an amount of about 225 mg, caffeine in present in an amount of about 52 mg, N3-PUFA is present in an amount of about 100 mg, vitamin C is present in an amount of about 50 mg, and ascorbyl palmitate is present in an amount of about 60 mg.

In some embodiments, the oral ingestible medicament is administered to a subject two to four times each day. In some embodiments, the oral ingestible medicament is a capsule, a chewable tablet, a stick pack, or a sachet.

In some embodiments are provided methods of using flavonoid compositions for the treatment, prevention, improvement, or amelioration of a disorder, disease or disease state. In some embodiments, the disorder, disease or disease state is a heart disease, diabetes, hypertension, allergic reactions, asthma, arthritis, cancer, prostate diseases, and oxidative stress. In some embodiments are provided methods of using flavonoid compositions for the improvement of health or performance, including the improvement of athletic performance, improved bone health, strengthened immune response, prevention of fatigue, reduction in recovery time following exercise, and for boosting energy. In some embodiments, the flavonoid compositions improve performance by increasing mitochondrial biogenesis, increasing endurance, increasing strength, and/or increasing performance. In some embodiments, the flavonoid compositions are administered to a subject before, during, and/or after exercise.

Accordingly, in some embodiments is provided a method for improving health or performance in a subject. In some embodiments, the method includes administering to the subject an oral ingestible medicament or flavonoid composition as described herein.

In some embodiments is provided method for treating, ameliorating, or improving a disorder in a subject, or improving the performance of a subject, includes administering to the subject an oral ingestible medicament or flavonoid composition as described herein.

In some embodiments, the disorder is heart disease, diabetes, hypertension, allergic reactions, asthma, arthritis, cancer, prostate diseases, and oxidative stress, or combinations thereof In some embodiments, the performance of the subject includes improvement in one or more of athletic performance, bone health, immune response, recovery time after exercise, oxidative stress, and energy.

In some embodiments, administration of an oral ingestible medicament or flavonoid composition as described herein increases the total urinary phenolic concentration, the dietary flavonoid intake, the dietary anthocyanin, the dietary EGCG, or the dietary quercetin. In some embodiments, administration of an oral ingestible medicament or flavonoid composition as described herein reduces the risk of mortality, neurodegenerative diseases, weight gain, systemic inflammation, oxidative stress, diabetes, cardiovascular disease, hypertension, or acute respiratory illness. In some embodiments, administration of an oral ingestible medicament or flavonoid composition as described herein improves colon health. In some embodiments, administration of an oral ingestible medicament or flavonoid composition as described herein improves colon microbiome.

Some embodiments herein relate to a chewable tablet including quercetin, bilberry extract, green tea leaf extract, and one or more of vitamin C, caffeine, or omega 3 fatty acids. In some embodiments herein relate to a chewable tablet including vitamin C, wild bilberry fruit extract, green tea leaf extract, quercetin aglycone, caffeine, and omega 3 fatty acids. In some embodiments, vitamin C is present as ascorbyl palmitate. In some embodiments, vitamin C is present in an amount of about 100 mg. In some embodiments, the wild bilberry fruit extract comprises about 25% total anthocyanins. In some embodiments, the green tea leaf extract comprises about 50% epigallocatechin 3-gallate (EGCG). In some embodiments, the omega 3 fatty acids comprise n3 polyunsaturated fatty acids (n3-PUFA). In some embodiments, the n3-PUFA is present in an amount of about 60 mg. In some embodiments, the n3-PUFA comprises docosahexaenoic acid and eicosapentaenoic acid. In some embodiments, the docosahexaenoic acid is present in an amount of about 24 mg. In some embodiments, the eicosapentaenoic acid is present in an amount of about 36 mg. In some embodiments, the caffeine is present in an amount of about 107 mg. In some embodiments, the composition comprises about 329 mg of total flavonoids in aglycone form. In some embodiments, the tablet further includes one or more of sugar, natural and artificial flavors, cellulose gum, sucralose, bamboo whole plant extract, guar gum, xanthan gum, citric acid, malic acid, or L-tartaric acid. In some embodiments, vitamin C is present in an amount of about 100 mg, the omega 3 fatty acids are present in an amount of about 60 mg, the caffeine is present in an amount of about 107 mg, and total flavonoids are present in an amount of about 329 mg. In some embodiments, the chewable tablet is administered to a subject at a dose of two tablets twice daily. In some embodiments, the chewable tablet is administered to a subject prior to a meal.

Some embodiments relate to a method of improving flavonoid bioavailability and bioactivity in a subject. In some embodiments, the method includes administering the chewable tablet as described herein to the subject. In some embodiments, the total flavonoid intake is increased.

Some embodiments relate to a method of increasing gut-derived phenolics in a subject. In some embodiments, the method includes administering a chewable tablet as described herein to the subject. In some embodiments, increased gut-derived phenolics include one or more of 1,2,3-benzenetriol sulfate, 3-methoxycatechol sulfate, 3-(3-hydroxyphenyl)propanoic acid sulfate, 3-hydroxyhippurate, or 4-methylcatechol sulfate.

BRIEF DESCRIPTION OF THE DRAWINGS

In order to describe the manner in which the above-recited and other advantages and features of the invention can be obtained, a more particular description will be rendered by reference to specific embodiments thereof which are illustrated in the appended drawings. Understanding that these drawings depict only typical embodiments and are not therefore to be considered to be limiting of its scope, the invention will be described and explained with additional specificity and detail through the use of the accompanying drawings in which:

FIG. 5A depicts dietary flavonoid concentration. FIG. 5B depicts dietary epigallocatechin 3-gallate (EGCG) concentration. FIG. 5C depicts dietary anthocyanin concentration. FIG. 5D depicts dietary quercetin concentration.

FIG. 10A shows the increases of 3-methoxycatechol sulfate (p=0.015). FIG. 10B shows the increases in 3-(3-hydroxyphenyl)propionoic acid sulfate (p=0.050). FIG. 10C shows the increases in 1,2,3-benzenetriol sulfate (p=0.030). All graphs show increases of gut-derived phenolics from left to right as: flavonoid pre-study; flavonoid after 12 weeks; placebo pre-study; and placebo after 12 weeks.

DETAILED DESCRIPTION

Figure 1:
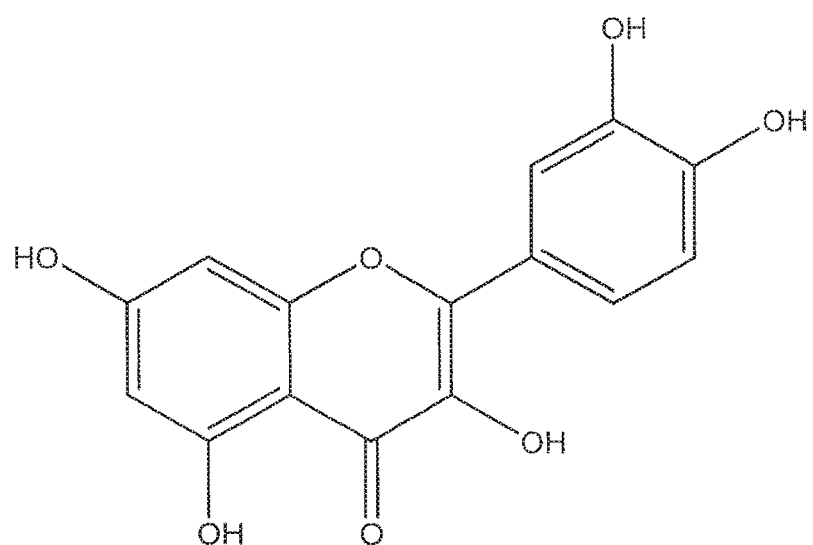
FIG. 1 illustrates a chemical drawing of an exemplary quercetin, wherein the quercetin is aglycone quercetin.

In some embodiments, the present application discloses flavonoid compositions and methods of using these flavonoid compositions. In other embodiments, the compositions and methods comprise compositions containing quercetin. In yet other embodiments, the methods comprise methods of preparing compositions containing quercetin. In some instances, the methods comprise methods of administering a composition of quercetin to a human and/or animal subject. The composition containing quercetin can comprise any effective amount of quercetin. The composition containing quercetin can also comprise one or more additive components configured to modulate the bioavailability, absorption, distribution, metabolism, and/or excretion of quercetin to increase a therapeutic effect of quercetin on the human and/or animal subject.

The term "subject" includes animals (for example, mammals, for example, cats, dogs, horses, pigs, cows, sheep, rodents, rabbits, squirrels, camels, bears, primates (for example, chimpanzees, gorillas, and humans)) It also includes transgenic animal models.

In some embodiments, polyphenols, flavonoids, flavonols, and quercetin are reported to provide health benefits. As described herein, polyphenols, flavonoids, flavonols, and quercetin are shown to prevent and/or treat heart disease, to help treat diabetes, to prevent and/or treat hypertension, to treat allergic reactions, to treat asthma, to treat arthritis, to prevent and/or treat cancer, to alleviate prostate problems, to improve athletic performance, to improve bone health, to strengthen immune response, to prevent fatigue, to reduce recovery time after exercise, to counter oxidative stress, and/or to boost energy.

In some embodiments, polyphenols, flavonoids, flavonols, and quercetin are administered to help athletes before, during, and/or after exercise. Polyphenols, flavonoids, flavonols, and quercetin can help athletes by increasing mitochondrial biogenesis, increasing endurance, and/or increasing performance.

As used herein, the term "polyphenols" refers to a compound containing more than one phenolic hydroxyl group. Polyphenols are a structural class of mainly natural, but also synthetic or semisynthetic organic chemicals characterized by the presence of large multiples of phenol structural units. Polyphenols are a classification of colorful phenolic organic compounds found in plants. As described herein, a high dietary intake of polyphenols reduce the risk for one or more of mortality, neurodegenerative diseases, weight gain, systemic inflammation and oxidative stress, diabetes, cardiovascular disease, hypertension, or acute respiratory illness.

As used herein, the term "flavonoids" refers to a group of plant metabolites that provide health benefits through cell signaling pathways and antioxidant effects. Flavonoids are polyphenolic molecules containing 15 carbon atoms and are soluble in water. Flavonoids are a subgroup within the polyphenols and function as natural antioxidants.

The flavonoid subgroup can be divided into six smaller groups including flavonols. As used herein, the term "flavonol" refers to phytochemical compounds found in high concentrations in a variety of plant-based foods and beverages. Based on their structure, they are classified as flavonoids and include the following compounds: quercetin, kaempferol, and myricetin.

As used herein, the term "quercetin" refers to a yellow crystalline pigment present in plants, and is used as a food supplement to reduce allergic responses or to boost immunity. Quercetin belongs to the flavonol group and can be found in a wide variety of fruits and vegetables. Quercetin can be found at least in the following fruits and vegetables: capers, lovage, dock like sorrel, radish leaves, carob fiber, dill, cilantro, Hungarian wax pepper, fennel leaves, red onion, radicchio, watercress, buckwheat, kale, chokeberry, cranberry, lingonberry, black plums, cow peas, sweet potato, blueberry, sea buckthorn berry, rowanberry, crowberry, prickly pear cactus fruits, red apples, broccoli, bilberry, tomatoes, black tea, and green tea. In some embodiments, pure quercetin may be extracted from the flowering genus of plants, *Uncaria*.

In some embodiments, flavonoids are derived from plant extracts, including from blueberry or bilberry fruit extracts. In some embodiments, flavonoids are derived from the genus of plants, *Vaccinium*.

In some embodiments, quercetin can refer to aglycone quercetin (or quercetin aglycone). FIG. 1 illustrates embodiments of aglycone quercetin. Aglycone quercetin can refer to the quercetin backbone without any bound glucosyl or polysaccharide groups. Aglycone quercetin can also be referred to as 2-(3,4-dihydroxyphenyl)-3,5,7-trihydroxy-4H-chromen-4-one. Aglycone quercetin can also be referred to as one or more of sophoretin, meletin, quercetine, xanthaurine, quercetol, quertine, and/or flavin meletin.

Figure 2:
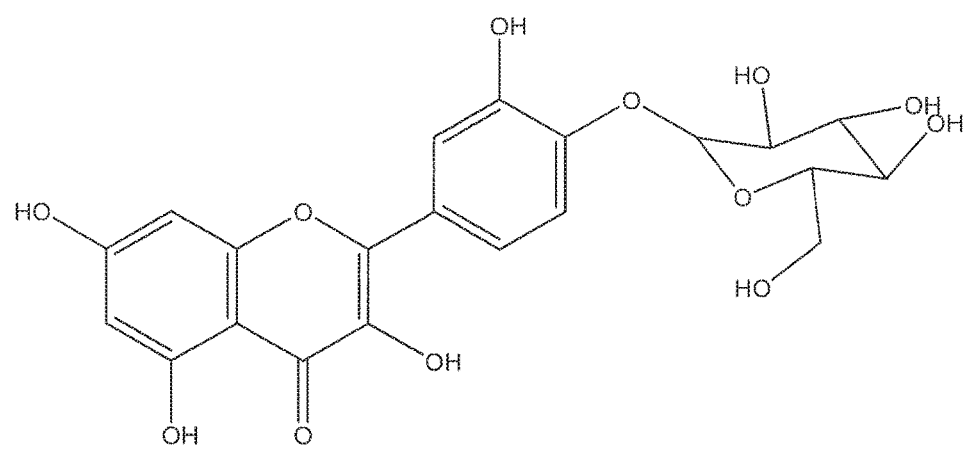
FIG. 2 illustrates a chemical drawing an exemplary quercetin 4'-glucoside.
Figure 3:
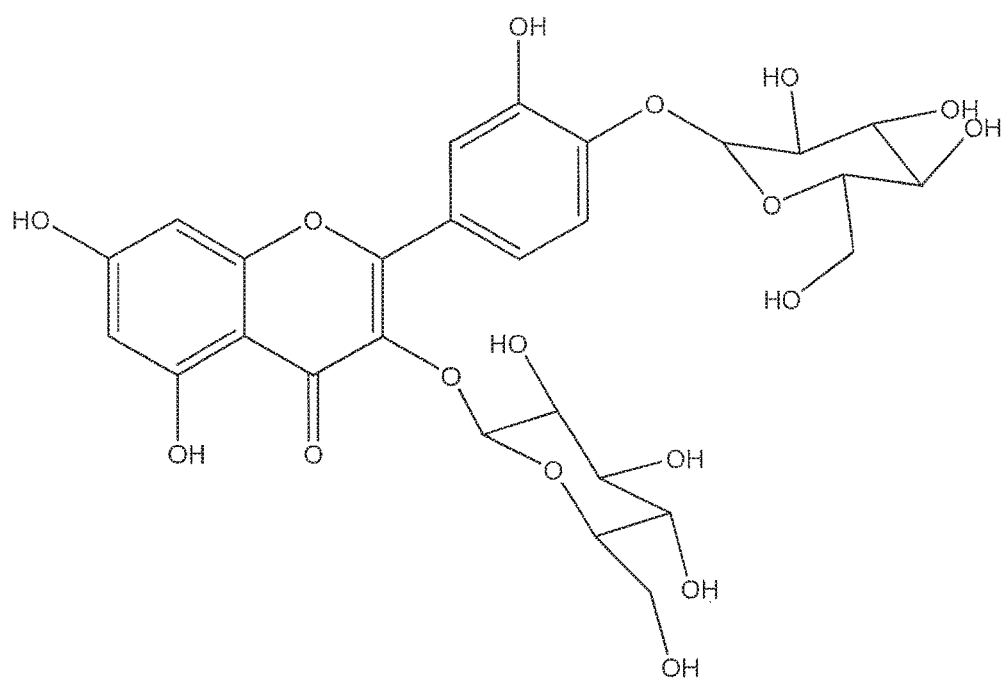
FIG. 3 illustrates a chemical drawing of an exemplary quercetin 3,4'-diglucoside.
Figure 4:
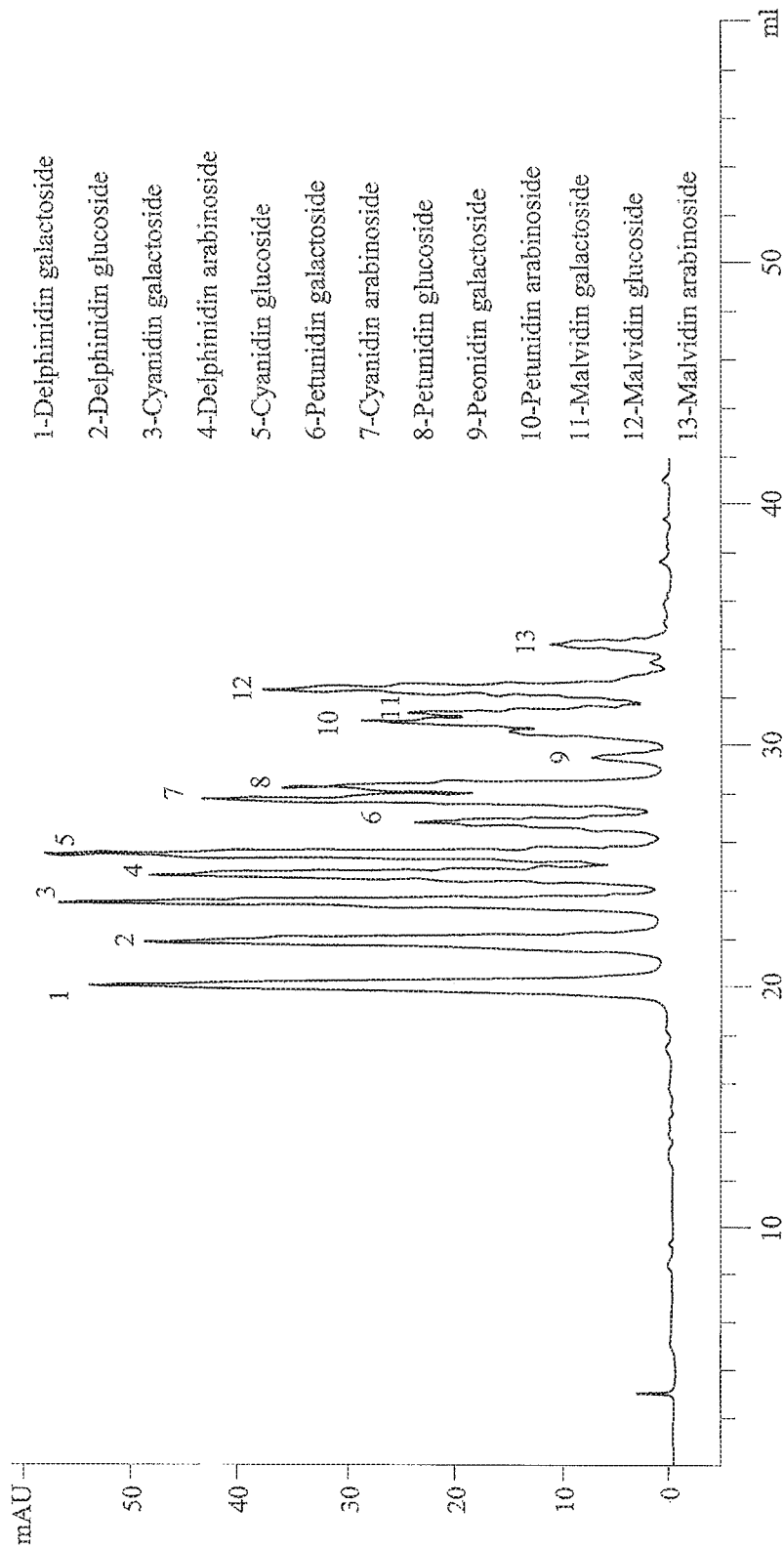
FIG. 4 depicts an exemplary chromatography profile of wild blueberry extract, identifying exemplary anthocyanidins that may be present in wild blueberry extracts.
Figure 5A:
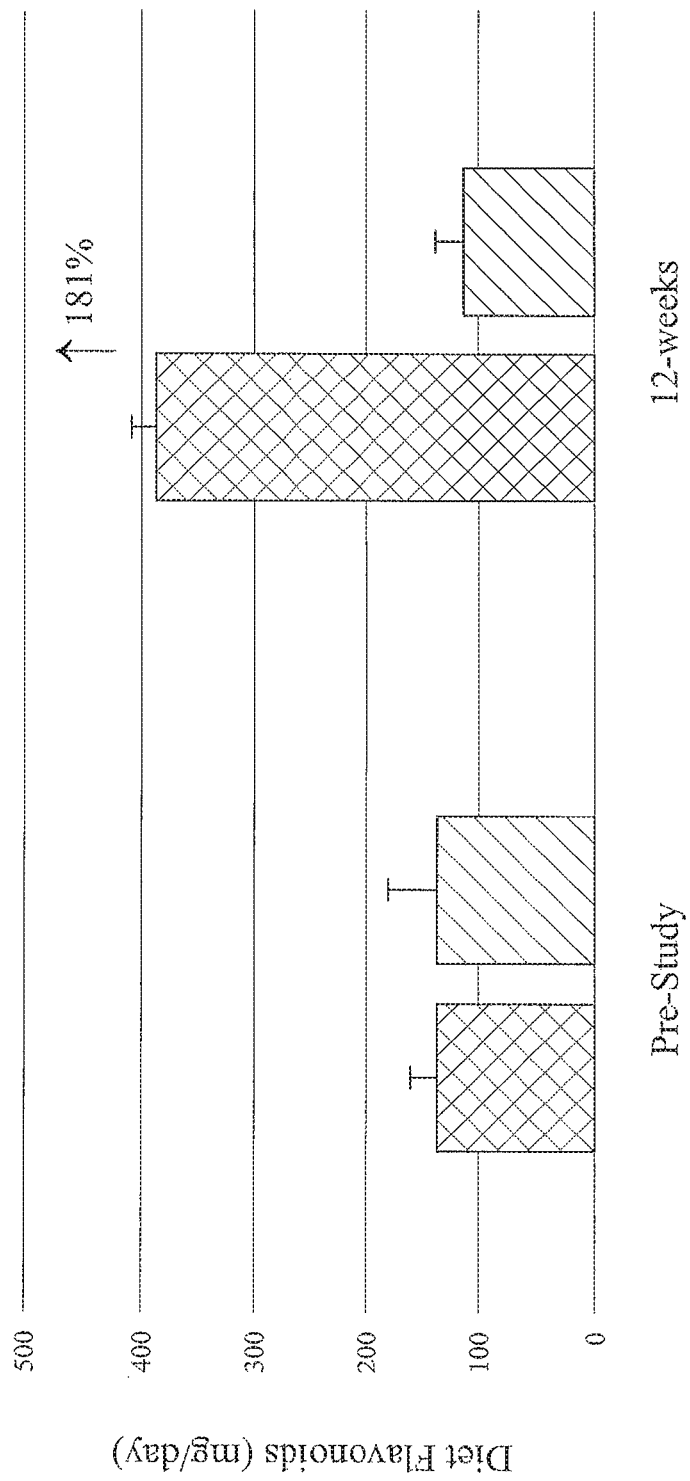
FIGS. 5A-5D graphically depict the concentration of metabolites in the test group (left; administered a flavonoid composition) and the control group (right; administered placebo) prior to and at 12-weeks of administration of a flavonoid composition or placebo.
Figure 5B:
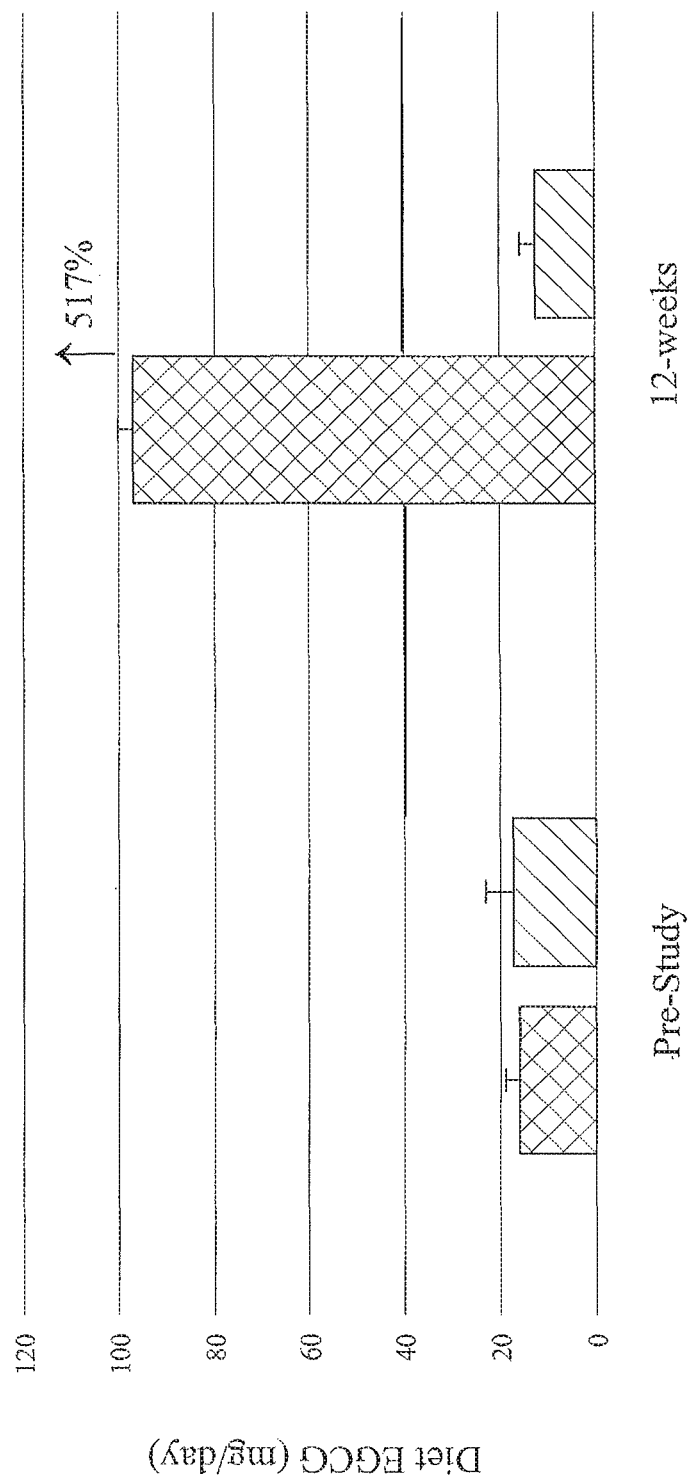
Figure 5C:
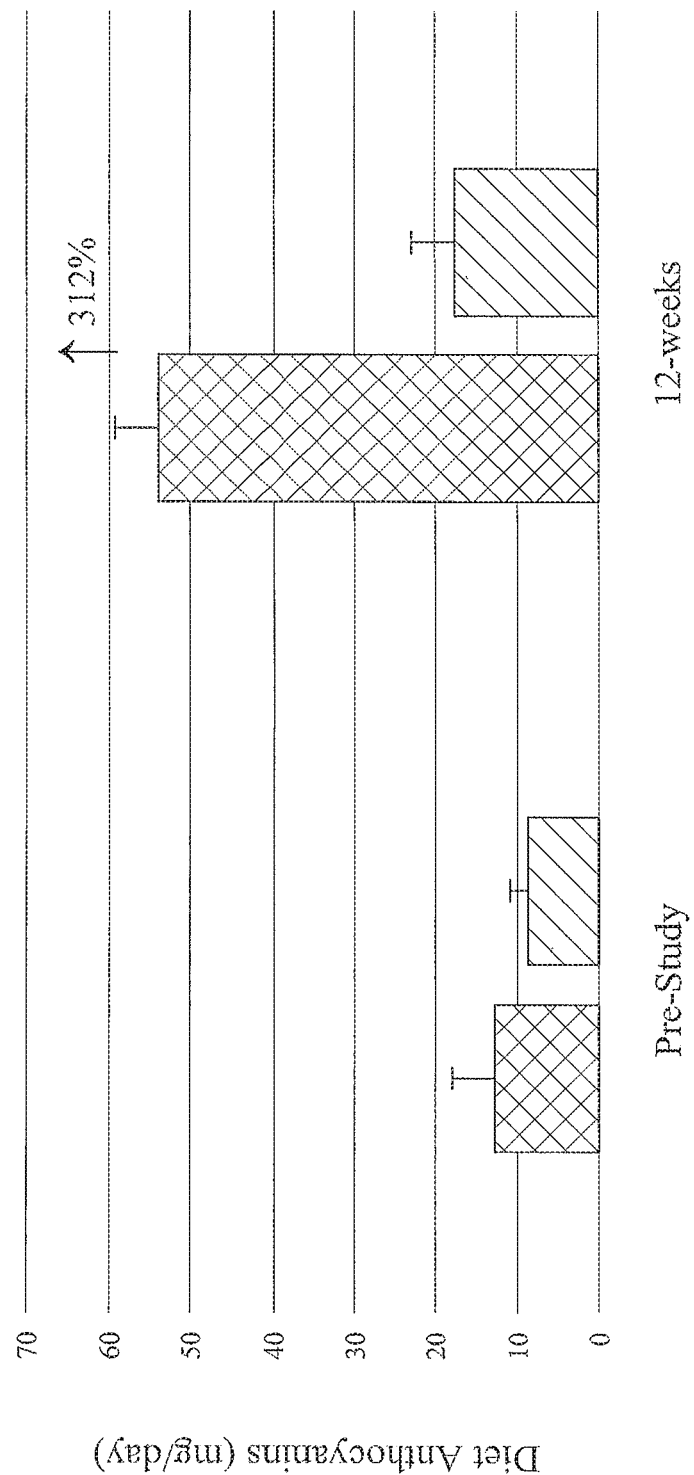
Figure 5D:
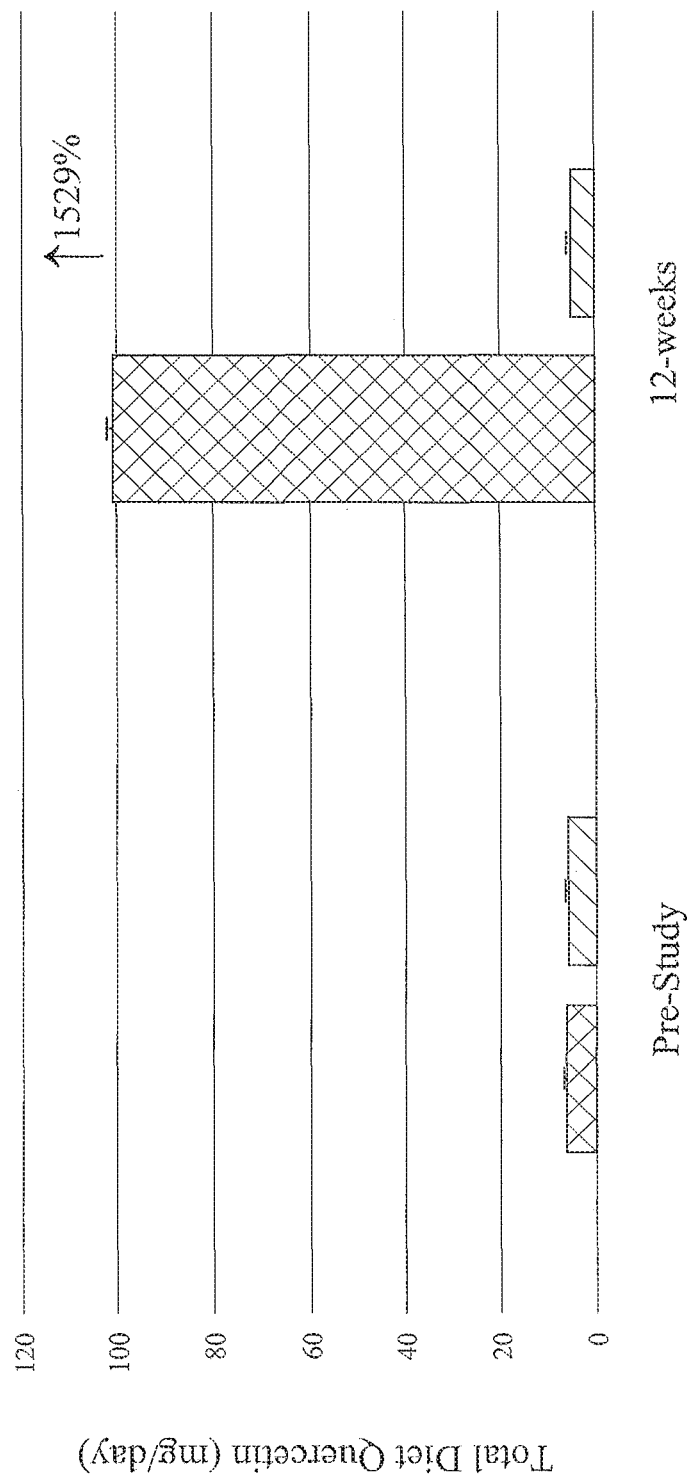

In some embodiments, quercetin refers to quercetin glucosides. Naturally occurring forms of quercetin can include quercetin glycosides. Quercetin glycosides can include rutin, (for example, rutoside, sophorin, and quercetin-3-O-rutinoside). Quercetin glycoside can also include quercitrin, which is a 3-O-a-L-rhamnoside. Quercetin glycoside can also include guaijaverin, which is a 3-O-arabinoside. Quercetin glycoside can also include hyperoside, which is a 3-O-galactoside. Quercetin glycoside can also include isoquercetin, which is a 3-O-glucoside. Quercetin glycoside can also include spiraeoside, which is a 4'-O-glucoside. Quercetin glycoside can also include miquelianin, which is a quercetin 3-O—B-d-glucuronopyranoside. FIG. 2 illustrates a quercetin glycoside, quercetin 4'-glucoside. FIG. 3 illustrates a quercetin glycoside, quercetin 3,4'-diglucoside.

In some embodiments, quercetin comprises any aglycone quercetin, any quercetin glycoside, and/or any quercetin derivative. Quercetin can be derived from any appropriate plant-based source. Quercetin can comprise any plant-based extract that is enriched in any aglycone quercetin, any quercetin glycoside, and/or any quercetin derivative. Quercetin can be extracted, isolated, and/or enriched by any appropriate methods as known in the art. Quercetin can comprise a mixture further comprising one or more of polyphenols, flavonoids, and/or flavonols.

In some embodiments, quercetin can have a generally low bioavailability upon ingestion. The generally low bioavailability can possibly be due to low absorption, rapid metabolism, and/or rapid elimination after ingestion. In other embodiments, absorption can be affected by differences in glycosylation, the makeup of the food matrix that contains the quercetin, and/or co-consumption of other food components such as fiber. In yet other embodiments, quercetin bioavailability increases with co-ingestion of other food components such as fats. In some cases, pure quercetin aglycone is absorbed differently than quercetin glycosides. In other cases, quercetin glycosides such as isoquercetin are more completely absorbed than quercetin aglycone. In some instances, simultaneous ingestion of quercetin with additives such as vitamin C, folate, and/or additional flavonoids improves the bioavailability of quercetin. Quercetin has a half-life of about 3.5-11 hours, and accumulates in the lungs, kidneys, heart, and liver.

The term "bioavailability" includes, generally, the degree to which a drug or other substance becomes available to a subject following ingestion, administration, or exposure. In one embodiment, for example, the bioavailability of the quercetin compounds may be the bioavailability to a particular target tissue. For example, in an embodiment, the particular target tissue may require traversal of the stomach or the small intestines, therefore the bioavailability data may be obtained from this particular target tissue.

The term "bioactive" includes, generally, to a property or characteristic of a substance, molecule, agent, or formulation or component thereof, having a biological effect.

In some embodiments, the bioavailability and bioactive influences of individual flavonoids are potentiated when mixed with other flavonoids or included with other polyphenols, nutrients, and omega-3 fatty acids. In some embodiments, n3-PUFa enhances both the bioavailability and bioactive effects of the flavonoids and flavonoid formulations provided herein. In some embodiments, n3-PUFA enhances the bioavailability and bioactive effects of quercetin.

The majority of dietary polyphenol intake reaches the colon. Polyphenols are subject to microbial degradation in the colon, converting polyphenols to simple phenols, and improving colon health and microbiome. Phenols can then be reabsorbed into the portal vein, which can be augmented with exercise, to the liver. In the liver, phenols undergo phase II biotransformation. The product is then released into circulation, where it exerts a beneficial bioactive effect before being excreted in the urine. As an example, the polyphenol, cyaniding, is converted to hydroxybenzoic acid by microbial degradation in the colon. Hydroxybenzoic acid is converted to hippuric acid through phase-2 conjugation. Hippuric acid is released into the bloodstream, and is eventually excreted in the urine. A high urine phenolic content reflects a high diet intake of polyphenols, and is linked to 30% lower mortality. Furthermore, a high diet consumption of flavonoids is associated with reduced risk of mortality in older women of about 60%. In some embodiments, a flavonoid formulation can provide an increase in urine total phenolics and in gut-derived phenolic metabolites.

In some embodiments, the flavonoid composition comprises one or more active ingredients, including: 100 mg quercetin, quercetin analogue and/or derivative, or preferably isoquercetin, or combinations thereof (for example, at least about 50% each of quercetin and isoquercetin), 90-180 mg epigallocatechin 3-gallate (EGCG) with green tea extract, 120-240 mg blueberry anthocyanidins from extract, 100 mg caffeine, 100 mg N3-PUFA (60 mg DHA, 40 mg EPA), and 100 mg vitamin C In other embodiments, the flavonoid composition comprises any other additive that is effective for increasing the bioavailability of the quercetin.

In some embodiments, the flavonoid composition includes quercetin aglycone or an analogue or derivative thereof, green tea leaf extract (50% EGCG), bilberry fruit extracts (25% total anthocyanins), caffeine, n3-PUFA (a mixture of docosahexaenoic acid and eicosapentaenoic acid), and vitamin C (as ascorbyl acetate).

In some embodiments, the flavonoid composition includes a flavonoid other than or in addition to quercetin, for example, one or more flavonoid as described in Table 1 or other flavonoid. Thus, the flavonoid composition can include one or more of quercetin, kaempferol, myricetin, isorhamnetin, luteolin, apigenin, hesperetin, naringenin, eriodictyol, catechins, epigallocatechins, theaflavins, cyaniding, delphinidin, malvidin, pelargonidin, peonidin, petunidin, daidzein, genistein, or glycitein. In some embodiments, the flavonoid is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, the flavonoid is present in an amount of about 52 mg. In some embodiments, the total flavonoids present in the composition is in an amount of about 329 mg.

In some embodiments, the flavonoid composition further comprises an antioxidant. As used herein, the term "antioxidant" refers broadly to a molecule that inhibits the oxidation of other molecules. In some embodiments, an antioxidant, as used herein, refers to green tea extract and its molecular components, which can include, for example, epigallocatechin (EGC), epicatechin gallate (ECG), epigallocatechin gallate (EGCG), epicatechin (EC), and flavonoids, such as kaempferol, quercetin, and myricetin. In some embodiments, the antioxidant is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, the antioxidant is present in an amount of about 90 mg. In some embodiments, the antioxidant is present as green tea leaf extract having 1, 2, 3, 4, 5, 10, 15, 20, 25, 30, 35, 40, 45, 50, 55, 60, 65, 70, 75, 80, 85, 90, 95, or 100% EGCG. In some embodiments, the antioxidant is present as green tea leaf extract having about 50% EGCG.

In some embodiments, the flavonoid composition includes an anthocyanin. As used herein, the term "anthocyanin" refers to a class of flavonoids obtained from tissues of plants, including from blueberry or bilberry fruit extracts. In some embodiments, the anthocyanin is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, the anthocyanin is present in an amount of about 225 mg. In some embodiments, the anthocyanin is a bilberry fruit extract having an amount of 1, 2, 3, 4, 5, 10, 15, 20, 25, 30, 35, 40, 45, 50, 55, 60, 65, 70, 75, 80, 85, 90, 95, or 100% total anthocyanin, or a percentage within a range defined by any two of the aforementioned percentages. In some embodiments, bilberry fruits extract is present having an amount of about 25% total anthocyanins.

In some embodiments, the flavonoid composition further comprises an anthocyanidin. As used herein, the term "anthocyanidin" refers to a plant pigment from a plant extract, and is a sugar-free counterpart of anthocyanins. In some embodiments, an anthocyanidin can be obtained from a plant, including from blueberry extracts. In some embodiments, anthocyanidins include, for example, apigeninidin, aurantinidin, capensinidin, cyanidin, delphinidin, europinidin, hirsutidin, luteolinidin, malvidin, pelargonidin, peonidin, petunidin, pulchellidin, rosinidin, or triacetidin, or combinations thereof. In some embodiments, the anthocyanidin is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, the anthocyanidin is present in an amount of about 225 mg.

In some embodiments, the flavonoid composition further comprises a stimulant. As used herein, the term "stimulant" refers to pharmaceutically active compounds that temporarily increase the rate of body functions. Stimulants can include, for example, amineptine, amiphenazole, amphetamines, bromantan, caffeine, carphedon, cocaine, ephedrines, fencamfamine, mesocarb, pentylentetrazol, pipradol, salbutamol, salmeterol, terbutaline, and related substances. In some embodiments, the stimulant is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, the stimulant is present in an amount of about 52 mg. In some embodiments, the stimulant is present in an amount of about 107 mg.

In some embodiments, the flavonoid composition further comprises a lipid. As used herein, the term "lipid" refers to fatty acids and derivatives thereof, as well as substances related biosynthetically or functionally to such compounds. In some embodiments, lipids refers to n3 polyunsaturated fatty acids (N3-PUFA or n3-PUFA). In some embodiments, the lipid is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, the lipid is present in an amount of about 100 mg. In some embodiments, the lipid is present in an amount of about 60 mg. In some embodiments, the lipid is present as n3-PUFA. In some embodiments, n3-PUFA is a combination of docosahexaenoic acid and eicosapentaenoic acid. In some embodiments, docosahexaenoic acid is present in an amount of about 24 mg and eicosapentaenoic acid is present in an amount of about 36 mg.

In some embodiments, the flavonoid composition further comprises ascorbic acid. Ascorbic acid refers to one form of vitamin C, and derivatives or analogues thereof. In some embodiments, ascorbic acid is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, ascorbic acid is present in an amount of about 50 mg. In some embodiments, ascorbic acid is present as vitamin C in an amount of about 100 mg.

In some embodiments, the flavonoid composition further comprises omega 3 fatty acids. Omega 3 fatty acids can be prepared in powder formulations and can include, for example, eicosapentaenoic acid, docosahexaenoic acid, linolenic acid, hexadecatrienoic acid, stearidonic acid, eicosatrienoic acid, eicosatetraenoic acid, heneicosapentaenoic acid, docosapentaenoic acid, tetracosapentaenoic acid, or tetracosahexaenoic acid, or analogues or derivatives thereof, or combinations thereof. In some embodiments, the omega 3 fatty acid is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, the omega 3 fatty acid is present in an amount of about 100 mg.

In some embodiments, the flavonoid composition further comprises ascorbyl palmitate. In some embodiments, ascorbyl palmitate is present in an amount of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg or greater, or a value within a range defined by any two of the aforementioned values. In some embodiments, the ascorbyl palmitate is present in an amount of about 60 mg. In some embodiments, ascorbyl palmitate is formed from ascorbic acid and palmitic acid creating a fat-soluble form of vitamin C. In some embodiments, ascorbyl palmitate is present in an amount of about 100 mg.

Accordingly, in some embodiments, the flavonoid composition includes a flavonoid (10-500 mg, for example 52 mg), an antioxidant (10-500 mg, for example 90 mg), an anthocyanidin (10-500 mg, for example 225 mg), a stimulant (10-500 mg, for example 52 mg), a lipid (10-500 mg, for example, 100 mg), ascorbic acid (10-500 mg, for example, 50 mg), an omega 3 fatty acid (10-500 mg, for example, 100 mg), and ascorbyl palmitate (10-500 mg, for example, 60 mg). The compositions may have one or more of the aforementioned components in a range of quantities. The quantities vary depending on the circumstance, requirements, or purpose of the specific formulation. Thus, for example, one formulation may require a greater quantity of any one or more component than a different formulation. Thus, the provided quantities are given by way of example only and are not intended to be limiting in scope.

In some embodiments, the additive is used to enhance bioavailability of the flavonoid or of quercetin, and thus the additive is a bioavailability enhancing agent. The term "bioavailability enhancing agent" includes agents that, when administered in combination with quercetin, increase the availability of the quercetin compound in the subject. Suitable bioavailability enhancing agents include, for example, charge masking compounds, solubilizing compounds, reducing compounds, stabilizing compounds, lubricating compounds, enteric coatings, permeability enhancing compounds, or combinations thereof. Thus, the bioavailability enhancing agent can include, for example, polysorbate 80 (TWEEN-80), ethylenediaminetetraacetic acid (EDTA), sodium bisulfite, octanol, oil, ethanol, calcium chloride, or silicon dioxide, or combinations thereof. In some embodiments, the formulations provided herein enhance the bioavailability and the bioactivity effects of quercetin.

In some embodiments is provided a therapeutic composition comprising a therapeutically effective amount of a quercetin compound in combination with a bioavailability enhancing agent and a pharmaceutically acceptable carrier for administration of said quercetin compound to the intestinal tract. The bioavailability enhancing agent and the quercetin compound may be administered concurrently in separate or in the same therapeutic composition.

The language "effective amount" of the quercetin compound is that amount necessary or sufficient to treat a subject, or to provide improvement, benefit, or enhancement to health or performance. The effective amount can vary depending on such factors as the size and weight of the subject, the type of result or outcome, or the particular quercetin compound. For example, the choice of the quercetin compound can affect what constitutes an "effective amount". One of ordinary skill in the art would be able to study the aforementioned factors and make the determination regarding the effective amount of the quercetin compound without undue experimentation.

In yet other embodiments, the flavonoid composition can comprise a pH of about 3 to about 4 to increase flavonoid stability. In some embodiments, the flavonoid composition comprises active ingredients configured to act synergistically to increase the bioavailability of quercetin. For example, vitamin C can act to increase the bioavailability of quercetin.

In some embodiments, the flavonoid composition comprises one or more active ingredients, including: about 16% (w/w) quercetin or an analogue or derivative thereof, or a combination thereof, including, for example, isoquercetin (or 50% each), about 15% to about 30% EGCG with green tea extract, about 20-40% (w/w) blueberry anthocyanidins from extract, about 16% (w/w) caffeine, about 16% (w/w) 100 mg N3-PUFA (60% DHA, 40% EPA), and about 16% vitamin C.

In some embodiments, the flavonoid composition comprises one or more non-active ingredients. In other embodiments, the non-active ingredients are configured to act as an inert carrier for the active ingredients. In yet other embodiments, the non-active ingredients can include one or more of: Domino Sugar Direct Compressible (Batory); Dextrose (Agglomerated); Flavor (Masking Type N&A) FCI 58002155; Flavor (Nat. Birthday Cake) Carmi 25193; Flavor (FLAVOR SWEET (A NATURAL FLAVOR)—FCI #40018125; Flavor (Vanilla N&A) Gold Coast #310119; Natural Bitterness Suppressor; Flavor (RASPBERRY—NAT & ART)—FCI #79028114; Natural Bamboo Silica; Sucralose; Flavor (Blueberry N&A)—FCI #12001135; Citric Acid Anhydrous; Flavor (Acai—N&A) FCI #10001154; DL-Malic Acid, L-Tartaric Acid, natural and artificial flavors, cellulose gum, bamboo whole plant extract, guar gum, or xanthan gum.

In some embodiments, the flavonoid composition comprises a form that is configured to be readily ingested by a human and/or animal subject. For example, the flavonoid composition can comprise a chew tablet that can be readily chewed to be ingested. In other cases, the flavonoid composition comprises a pill or tablet. In other instances, the flavonoid composition comprises a gummy chew. In yet other cases, the flavonoid composition can comprise a dissolvable strip or a thick goo-like form. In other embodiments, the flavonoid composition is configured as a slow-release or extended-release formulation.

In some embodiments, the flavonoid composition is configured as a chew tablet and is configured to be consumed with an aqueous carbohydrate source. The aqueous carbohydrate source can comprise a 2:1 glucose to fructose ratio. In other embodiments, the flavonoid composition is configured as a single chew tablet that comprises 100 mg quercetin or preferably isoquercetin (or 50% each), 90-180 mg EGCG with green tea extract, 120-240 mg blueberry anthocyanidins from extract, 100 mg caffeine, 100 mg N3-PUFA (60 mg DHA, 40 mg EPA), and 100 mg vitamin C Two to four of these single chew tablets can be administered to a subject per day. In yet other embodiments, the described single chew tablets act as a substitute for non-steroidal anti-inflammatory drugs (NSAIDs). In some embodiments, each tablet includes from 10-500 mg of flavonoid. In some embodiments, each tablet includes 10, 20, 30, 40, 50, 60, 70, 80, 90, 100, 120, 140, 160, 180, 200, 250, 300, 350, 400, 450, or 500 mg of flavonoid or greater, or an amount within a ranged defined by any two of the aforementioned values. In some embodiments, each tablet includes about 70 mg of flavonoid. In some embodiments, four tablets are administered daily. In some embodiments, the total daily administration includes about 280 mg of flavonoid. In some embodiments, two tablets are taken at a given time, twice daily.

Flavors are additives that give food a particular taste or smell, and may be derived from naturally occurring ingredients or prepared synthetically. In some embodiments, the flavor may include chocolate, vanilla, cola, coffee, latte, cappuccino, butterscotch, almond, mint, peach, grape, pear, passion fruit, pineapple, banana or banana puree, apricot, citrus, orange, lemon, grapefruit, apple, cranberry, tomato, mango, papaya, lime, tangerine, cherry, blueberry, strawberry, raspberry, coconut, carrot and/or mixtures thereof.

As used herein, the term "treatment" refers to an intervention made in response to a disease, disorder or physiological condition manifested by a subject, particularly a subject suffering from one or more of a disorder, disease or disease state. In some embodiments, the disorder, disease or disease state is a heart disease, diabetes, hypertension, allergic reactions, asthma, arthritis, cancer, prostate diseases, and oxidative stress. In some embodiments, the treatment refers to the improvement of health or performance, including the improvement of athletic performance, improved bone health, strengthened immune response, prevention of fatigue, reduction in recovery time following exercise, and for boosting energy. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments, treatments reduce, alleviate, or eradicate the symptom(s) of the disease(s). In some embodiments, treatment can refer to enhancement of secondary effects of the disease, including enhancement or improvement of athletic performance. As used herein, the term "prevention" refers to any activity that reduces the burden of the individual later expressing disease symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. In some embodiments, the flavonoid formulations described herein have anticancer effects. In some embodiments, the combination of quercetin, green tea extract, vitamin C, and other micronutrients show improved anticancer efficacy in cell culture.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application, and administered in the form of a conventional therapeutic preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also include, for example, one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counter ions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers. Pharmaceutically acceptable carrier includes substances capable of being coadministered with the quercetin compound(s), and which allow both to perform their intended function.

The pharmaceutically acceptable or appropriate carrier may include other compounds known to be beneficial to an impaired situation of the GI tract, (for example, antioxidants, such as Vitamin C, Vitamin E, Selenium or Zinc); or a food composition. The food composition can be, but is not limited to, milk, yogurt, curd, cheese, fermented milks, milk based fermented products, ice-creams, fermented cereal based products, milk based powders, infant formulae, tablets, liquid bacterial suspensions, dried oral supplement, or wet oral supplement.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In certain embodiments, the "purity" of any given agent (for example, fulvate fraction, growth factor, etc.) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The term "solubility" refers to the property of a polyphenol, flavonoid, flavonol, quercetin, or other agent provided herein to dissolve in a liquid solvent and form a homogeneous solution. Solubility is typically expressed as a concentration, either by mass of solute per unit volume of solvent (g of solute per kg of solvent, g per dL (100 mL), mg/mL, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH. In certain embodiments, solubility is measured in water or a physiological buffer such as PBS. In certain embodiments, solubility is measured in a biological fluid (solvent) such as blood or serum. In certain embodiments, the temperature can be about room temperature (for example, about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/mL at room temperature or at 37° C.

Therapeutic Compositions

In some embodiments, the active ingredients and mixtures of active ingredients may be used, for example, in therapeutic compositions comprising a pharmaceutically acceptable carrier prepared for storage and subsequent administration. Also, some embodiments include use of the above-described active ingredients with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes and even flavoring agents may be provided in the therapeutic composition. For example, sodium benzoate, ascorbic acid and esters of p-hydroxybenzoic acid may be added as preservatives. In addition, antioxidants and suspending agents may be used.

Compositions of the active ingredients may be formulated and used as tablets, capsules, or elixirs for oral administration; suppositories for rectal administration; sterile solutions; patches for transdermal administration, and sub-dermal deposits and the like. Suitable excipients are, for example, water, saline, dextrose, mannitol, lactose, lecithin, albumin, sodium glutamate, cysteine hydrochloride, and the like. If desired, absorption enhancing preparations (for example, liposomes), may be utilized.

The compositions provided herein can be in the form of a dry powder. For example the dry powder can be in the form a shake mix or included in a capsule. For example, a dry powder composition provided herein can be mixed with a liquid (for example, water) to form a solution or aqueous slurry that can be consumed by a user as a beverage. In some cases, a dry powder composition provided herein can be packaged as a bulk product with or without a measuring spoon, as a single serving package containing an amount of a dry powder composition to be mixed with a liquid (for example, 4 ounces water, 6 ounces water, 8 ounces water, 12 ounces water). In some cases, a dry powder composition provided herein includes between 0.1 weight percent and 2.0 weight percent of one or more sweet potato extracts. In some cases, a dry powder composition provided herein includes between 5 weight percent and 85 weight percent protein. In some cases, a dry powder composition provided herein includes between 5 weight percent and 35 weight percent soluble fiber.

The compositions provided herein can include one or more additional ingredients. For example, a composition provided herein can include protein, carbohydrates, soluble fiber, flavorants, artificial sweeteners, preservatives, fillers, thickeners, colorants, and any other food safe additive. In some embodiments, the composition can include sugar, natural and artificial flavors, dextrose, cellulose gum, sucralose, bamboo whole plant extract, guar gum, xanthan gum, citric acid, malic acid, or L-tartaric acid. In some cases, a composition provided herein can include one or more fillers or thickeners selected from the following: a hydroxyl containing compound, a dextrin or dextrin derivative, carboxymethyl cellulose, hydroxypropyl cellulose, hydroxyethyl cellulose, hydroxypropyl methyl cellulose, methyl cellulose, calcium caseinate, konjac, collagen, inulin, casein, wheat gluten, carrageenan, alginates, propylene glycol alginate, xanthan, dextrin, pullulan, curdlan, gellan, locust bean gum, guar gum, tam gum, gum tragacanth, pectin, agar, zein, karaya, gelatin, *psyllium* seed, chitin, chitosan, gum acacia, polyvinyl pyrrolidone, polyethylene oxide, polyvinyl alcohol, or a combination thereof. In some cases, a composition provided herein can include between 0 and 5 weight percent thickener(s). In some cases, a composition provided herein can be substantially free of artificial colors, artificial flavors, and chemical preservatives.

The compositions provided herein can include one or more proteins. In some cases, a composition provided herein can include between 5 and 25 grams of protein (for example, about 10 grams of protein) per 8 fluid ounces of a beverage or for 30 grams of a powdered composition provided herein. In some cases, a composition provided herein can be in a powdered form and include between 5 weight percent and 85 weight percent protein(s) (for example, between 10 weight percent and 50 weight percent, between 15 weigh percent and 35 weight percent, between 30 weigh percent and 60 weight percent, or between 10 weight percent and 20 weight percent). For example, a composition provided herein can include between 10 weight percent and 13 weight percent of soy protein, between 8 weight percent and 10 weight percent whey protein concentrate, and/or between 5 weight percent and 7 weight percent whey protein isolate. Examples of proteins that can be included in a composition provided herein include dairy protein, soy protein, whey protein, or a combination thereof.

The compositions provided herein can be in the form of a beverage. A beverage composition provided herein can include a solution and/or a slurry. The composition provided herein can include additional ingredients such as fillers, thickeners, proteins, creamers, sweeteners, flavorants, or a combination thereof. In some case, a composition can include between 5 to 25 grams of protein per serving. In some case, a composition can include less than 10 grams of total fat per serving. In some case, a composition can include less than 5 grams of sugars per serving. In some case, a composition can include less than 10 grams of soluble fiber per serving. In some cases, a serving can be 8 ounces of a beverage composition or an amount of dry powder composition intended to be mixed with a liquid to form a single serving. For example, 8 ounces of water could be combined with about 30 grams of a dry powder composition provided herein to form a beverage composition. In some cases, a container or package containing a dry powder composition provided herein can include a measuring scoop or spoon sized to measure out a single serving of a dry powder composition provided herein.

Therapeutic preparations for oral use can be obtained by combining the active ingredients with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active ingredient doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active ingredient doses. Such formulations can be made using methods known in the art. See, for example, U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties. The therapeutic compositions may be manufactured in a manner that is itself known, for example, by means of conventional mixing, dissolving, granulating, dragee-making, levitating, emulsifying, encapsulating, entrapping, or lyophilizing processes.

To formulate the dosage including one or more active ingredients disclosed herein, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing ingredients, sweeteners, fragrances, colorants, preservatives and the like may be added to the administered formulation of the compound of the present disclosure, particularly when the compound is to be administered orally.

Further disclosed herein are various therapeutic compositions well known in the art for uses that include intraocular, intranasal, and intraauricular delivery. Therapeutic formulations include aqueous ophthalmic solutions of the active ingredients in water-soluble form, such as eyedrops, or in gellan gum (Shedden et al., Clin. Ther., 23(3):440-50 (2001)) or hydrogels (Mayer et al., Ophthalmologica, 210 (2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Frog. Clin. Biol. Res., 312:447-58 (1989)), and microspheres (Mordenti, Toxicol. Sci., 52(1):101-6 (1999)); and ocular inserts. All of the above-mentioned references are incorporated herein by reference in their entireties. Such suitable therapeutic formulations are most often and preferably formulated to be sterile, isotonic and buffered for stability and comfort. Therapeutic compositions may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Therapeutic formulations for intraauricular delivery include suspensions and ointments for topical application in the ear. Common solvents for such aural formulations include glycerin and water.

The compositions described herein may be administered by either oral or non-oral pathways. When administered orally, compositions can be administered in capsule, tablet, granule, spray, syrup, or other such form. Compositions also may be brewed, as with a tea, or formed by dissolving a powdered composition into a fluid, typically water, fruit or vegetable juice, or milk. When administered non-orally, it can be administered as an aqueous suspension, an oily preparation or the like or as a drip, suppository, salve, ointment or the like, when administered topically, rectally, or vaginally, as deemed appropriate by those of skill in the art.

In some embodiments, the compositions described herein are formulated into a single pill or tablet. In some embodiments, the pill or tablet has a mass from 10 mg to 2000 mg. In some embodiments, the pill or tablet has a mass from 100 mg to 1500 mg. In some embodiments, the pill or tablet has a mass from 500 mg to 1200 mg. In some embodiments, the pill or tablet has a mass from 800 mg to 1100 mg.

The compositions provided herein can include an artificial sweetener. For example, a composition provided herein can include a high intensity sweetener, such as saccharine, sucralose, aspartame, acesulfame potassium, or combinations thereof. In some cases, a composition provided herein can be substantially free of hydrogenated or trans fats. In some cases, a composition provided herein can be substantially free of corn syrup. In some cases, a composition provided herein can be substantially free of artificial colors, artificial flavors, and chemical preservatives. In some cases, a composition provided herein can be substantially free of vitamins or mineral fortification.

Methods of Administration

Some embodiments also encompass methods for making and for administering the disclosed compositions. Such disclosed methods include, among others, (a) administration through oral pathways, which administration includes administration in capsule, tablet, granule, spray, syrup, or other such forms, (b) administration topically, (c) administration rectally, or (d) administration vaginally, as deemed appropriate by those of skill in the art for bringing the compound of the disclosure into contact with living tissue; and (e) administration via controlled released formulations, depot formulations. As further examples of such modes of administration and as further disclosure of modes of administration, disclosed herein are various methods for administration of the disclosed compositions including modes of administration through intraocular, intranasal, and intraauricular pathways.

The therapeutically effective amount of the ingredients disclosed herein required as a dose will depend on the route of administration and the physical characteristics of the specific human under consideration. The dose can be tailored to achieve a desired effect, but will depend on such factors as weight, diet, concurrent medication and other factors, which those skilled in the medical arts will recognize.

In practicing the methods of the disclosure, the products or compositions can be used alone or in combination with one another or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular ingredients employed, and the specific use for which these ingredients are employed. The determination of effective dosage levels, that is the dosage levels necessary to achieve the desired result, can be accomplished by one skilled in the art using routine therapeutic methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established therapeutic methods. In non-human animal studies, applications of potential products are commenced at higher dosage levels, with dosage being decreased until the desired effect is no longer achieved or adverse side effects disappear.

The dosage of active ingredient(s) may range broadly, depending upon the desired affects and the therapeutic indication. Typically, dosages of active ingredient(s) may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration is preferably oral on a daily or twice daily basis. Administration may include four tablets taken by mouth daily. In some embodiments, tablets may be administered during a meal time. In some embodiments, two tablets may be administered during a meal. In some embodiments, two tablets may be administered at breakfast and two at lunch.

The exact formulation, route of administration and dosage can be chosen in view of the consumer's condition. See for example, Fingl et al., in The Pharmacological Basis of Therapeutics, 1975, which is incorporated herein by reference in its entirety. The magnitude of an administrated dose may vary with the severity of a particular medical or physical condition and the route of administration. The severity of a condition may, for example, be evaluated, in part, by standard prognostic evaluation methods. Further, the dose and perhaps dose frequency may also vary according to the age, body weight, and response of the individual. A program comparable to that discussed above may be used in veterinary medicine.

The combined active ingredients in the compositions disclosed herein may be orally or non-orally administered to a human patient in the amount of about 10 mg/day to about 1,000 mg/day of the total active ingredients, and more preferably about 50 mg/day to about 400 mg/day of the total active ingredients at, one time per day or in other embodiments, over two to about ten times per day. Nonetheless, as will be understood by those of skill in the art, in certain situations it may be necessary to administer the active ingredients disclosed herein in amounts that excess, or even far exceed, the above-stated, preferred dosage range to treat effectively and aggressively a desired condition or characteristic.

Ingredients disclosed herein can be evaluated for efficacy and toxicity using known methods. For example, the toxicology of a particular compound or ingredient, or of a subset of the compounds, sharing certain chemical moieties, may be established by determining in vitro toxicity towards a cell line, such as a mammalian, and preferably a human, cell line. The results of such studies are often predictive of toxicity in animals, such as mammals, or more specifically, humans. Alternatively, the toxicity of particular compounds or ingredients in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including the conditions abated by the compounds or ingredients disclosed herein, including obesity. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound or ingredient in humans.

The active ingredients described above may be used alone or in combination with one another, or in combination with other therapeutic or diagnostic agents. These products can be utilized in vivo or in vitro. The useful dosages and the most useful modes of administration will vary depending upon the age and weight of the consumer, the particular ingredients employed, and the specific use for which these ingredients are employed.

Methods of Use

The compositions described herein may be used for increasing the bioavailability, absorption, distribution, metabolism, and/or excretion of quercetin. The compositions described herein may be used for the reduction of blood pressure and LDL cholesterol, or for the increase of athletic performance. Thus, in some embodiments, the compositions described herein are administered to a human with elevated blood pressure or elevated LDL cholesterol. In some embodiments, the compositions described herein are administered to a human for increasing athletic performance.

The following non-limiting examples are meant to describe the preferred methods of the invention using certain preferred embodiments of the invention. Variations in the details of the particular methods employed and in the precise compositions obtained will undoubtedly be appreciated by those of skill in the art.

EXAMPLES

Example 1

Flavonoid Chewable Tablet Formulation

The following example demonstrates an exemplary embodiment of a composition comprising a flavonoid, and formulated as a chewable tablet.

A flavonoid composition was prepared by combining the following active ingredients, in the listed amounts in Table 2:

TABLE 2

Flavonoid Chewable Tablet Composition

| Active Ingredient | milligrams | % (w/w) |
|---|---|---|
| Blueberry Extract | 225 | 33.9% |
| Caffeine | 52.5 | 7.9% |
| Vitamin C (as Ascorbic Acid) | 83.33 | 12.6% |
| Green Tea Extract | 90 | 13.6% |
| Omega-3 F30 Powder | 100 | 15.1% |
| Quercetin | 52.6 | 7.9% |
| Ascorbyl Palmitate | 60 | 9.0% |
| Total: | 663.43 | 100.0% |

The prepared flavonoid composition was then combined with the following non-active ingredients to prepare a chewable tablet: Domino Sugar Direct Compressible (Batory); Dextrose (Agglomerated); Flavor (Masking Type N&A) FCI 58002155; Flavor (Nat. Birthday Cake) Carmi 25193; Flavor (FLAVOR SWEET (A NATURAL FLAVOR)—FCI #40018125; Flavor (Vanilla N&A) Gold Coast #310119; Natural Bitterness Suppressor; Flavor (RASPBERRY—NAT & ART)—FCI #79028114; Natural Bamboo Silica; Sucralose; Flavor (Blueberry N&A)—FCI #12001135; Citric Acid Anhydrous; Flavor (Acai—N&A) FCI #10001154; DL-Malic Acid; and L-Tartaric Acid. The chewable tablet was configured to be administered at a dosage of two chewable tablets per dose.

Example 2

Flavonoid Tablet Formulation

The following example demonstrates an exemplary embodiment of a composition comprising a flavonoid, and formulated as a tablet.

A flavonoid composition was prepared by combining the following active ingredients, in the listed amounts in Table 3. The quantity of each ingredient was confirmed at four weeks and at twelve weeks.

TABLE 3

Flavonoid Tablet Composition

| Assay | Method | mg/one tablet | mg/four tablets |
|---|---|---|---|
| Total Phenolics (gallic acid equivalent) | Folin-Ciocalteu assay | 104.25 ± 1.4 | 417.0 ± 5.7 |
| Total Proanthocyanidin (procyanidin B2 equivalent) | DMAC assay | 15.1 ± 0.8 | 60.3 ± 3.1 |
| Total Anthocyanins (cyaniding-3-glucoside equivalent) | $HPLC_{520\,nm}$ | 16.3 ± 1.0 | 65.2 ± 4.0 (38.6 aglycone) |
| Epigallocatechin Gallate (EGCG) | $HPLC_{280\,nm}$ | 21.4 ± 1.3 | 85.6 ± 5.2 |
| Quercetin | $HPLC_{360\,nm}$ | 23.9 ± 2.1 | 95.6 ± 8.4 |
| Caffeine | $HPLC_{280\,nm}$ | 24.8 ± 1.1 | 99.1 ± 4.4 |

The ingredients were combined to prepare a tablet. The tablet serving size is four tablets, with the following per serving: 50 kilocalories, 12 grams of carbohydrate (4% of daily value), 10 grams of sugars, 100 mg of vitamin C (as ascorbyl palmitate; 167% of daily value), 156 mg of wild bilberry fruit extract (std. min 25% total anthocyanins), 180 mg green tea leaf extract, 100 mg of quercetin, 100 mg natural caffeine (from *Coffea Arabica* bean), and 200 mg NovoOmega® Omega-3 F30 powder (std. 30% omega-3 fatty acids (eicosapentaenoic acid and docosahexaenoic acid)). Additional ingredients may include sugar, natural and artificial flavors, dextrose, cellulose gum, sucralose, bamboo whole plant extract, guar gum, xanthan gum, citric acid, malic acid, and L-tartaric acid. The tablet more than doubles the normal flavonoid intake and provides a more diverse array of flavonoids than typical.

Alternative Flavonoid Formulations

Additional exemplary formulations and compositions are prepared by combining the following ingredients, in the listed amounts in Table 4. The quantity of each ingredient was confirmed at zero weeks and 12 weeks later. Table 4 lists the quantity in mg for four tablets.

TABLE 4

Alternative Flavonoid Composition

| Component | Method | 0 weeks | 12 weeks |
|---|---|---|---|
| Total Phenolics (gallic acid equivalent) | Folin-Ciocalteu assay | 452 ± 20.0 | 533 ± 8.0 |

TABLE 4-continued

Alternative Flavonoid Composition

| Component | Method | 0 weeks | 12 weeks |
|---|---|---|---|
| Total Anthocyanins (cyaniding-3-O-glucose equivalent) | $HPLC_{520\ nm}$ | 64.3 ± 1.7 | 62.8 ± 2.8 |
| Quercetin | $HPLC_{360\ nm}$ | 104 ± 6.2 | 97.6 ± 8.8 |
| Total Flavan-3-ols | $HPLC_{280\ nm}$ | 184 ± 9.2 | 188 ± 10.8 |
| Epigallocatechin gallate (EGCG) | $HPLC_{280\ nm}$ | 88.4 ± 4.5 | 84.4 ± 5.2 |
| Epicatechin (EC) | $HPLC_{280\ nm}$ | 22.0 ± 2.4 | 24.0 ± 0.8 |
| Unknown flavan-ol (EGCG equivalent) | $HPLC_{280\ nm}$ | 40.4 ± 2.4 | 43.6 ± 2.0 |
| Epicatechin gallate (ECG) | $HPLC_{280\ nm}$ | 33.2 ± 0.8 | 35.2 ± 2.8 |
| Caffeine | $HPLC_{280\ nm}$ | 107 ± 6.8 | 98.6 ± 2.4 |

The ingredients were combined to prepare a tablet. The tablet serving size is four tablets, with the following per serving: 50 kilocalories, 12 grams of carbohydrate, 100 mg of vitamin C (as ascorbyl palmitate), bilberry fruit extract (std. min 25% total anthocyanins), green tea leaf extract (50% EGCG), quercetin aglycone, 107 mg caffeine, 60 mg n3-PUFA (24 mg as docosahexaenoic acid and 36 mg as eicosapentaenoic acid), and 329 mg total flavonoids (aglycone form). Additional ingredients include sugar (dextrose), natural and artificial flavors, cellulose gum, sucralose, bamboo whole plant extract, guar gum, xanthan gum, citric acid, malic acid, and L-tartaric acid.

Example 3

Influence of Ingesting a Flavonoid-Rich Supplement on the Human Metabolome and Concentration of Urine Phenolics The following example demonstrates the effects of ingesting a flavonoid-rich composition in overweight or obese subjects.

This study measures the effect of ingesting a flavonoid-rich supplement on various biomarkers in overweight/obese women during a 12-week period. The flavonoid-rich supplement contains a mixture of flavonoids including quercetin, catechins from green tea extract, and anthocyanins from blueberry extract, and other food components that facilitate flavonoid bioactivity including fish oil, caffeine, and vitamin C.

The primary objective of this study is to evaluate the effect of ingesting a flavonoid-rich supplement on total urine polyphenol concentration and shifts in blood metabolites related to flavonoid intake in healthy but overweight/obese community-dwelling adults. Subjects in the flavonoid supplement group achieve high urine polyphenol concentrations.

Secondary objectives are to determine related effects on measures of inflammation and oxidative stress. Chemistry profiles and symptom logs are compared pre- and post-study between groups to confirm prior safety data collected on human participants.

Subjects randomized to ingestion of the flavonoid-rich supplement compared to placebo will experience an increase in total urine polyphenols concentrations and shifts in blood metabolites related to increased flavonoid metabolism. Secondarily, subjects ingesting the flavonoid-rich supplement will experience a decrease in systemic inflammation and oxidative stress.

The following details demonstrate the effect of ingesting a flavonoid-rich supplement on blood metabolite shifts and urine phenolics during a 12-week period in overweight and/or obese women.

The characteristics for the control (placebo) group and test group (flavonoid composition) are provided in Table 5.

TABLE 5

Subject Characteristics

| | Flavonoid (N = 51) | | Placebo (N = 52) | | |
|---|---|---|---|---|---|
| | Mean | SD | Mean | SD | P-Value |
| Age (yr) | 50.3 | 11.2 | 50.3 | 14.0 | 0.986 |
| Height (in) | 63.9 | 2.0 | 64.5 | 2.5 | 0.199 |
| Weight (lbs) | 186 | 39.0 | 191 | 40.8 | 0.516 |
| Body Mass Index | 32.1 | 6.6 | 32.5 | 7.1 | 0.759 |
| Body Fat (%) | 42.0 | 7.3 | 41.9 | 7.4 | 0.972 |
| C-reactive protein (mg/L) | 4.66 | 4.8 | 4.89 | 5.5 | 0.823 |
| Glucose (mg/dL) | 95.7 | 15.9 | 96.4 | 17.5 | 0.855 |

Subjects were administered a flavonoid composition as described in Example 2 (flavonoid tablet) or a placebo, with 4 tablets each day for a 12-week period. Two tablets were administered at breakfast and two tablets were administered at lunch.

Prior to the study, subjects were asked to respond to a survey to determine their symptoms or feelings during the previous 4-week period. At the end of the study, the subjects were asked to complete the same survey. As shown in Table 6, subject responses were generally identical prior to and following the survey, indicating that the composition did not result in side effects.

TABLE 6

Intensity of Symptoms

| Symptom | Flavonoid pre-study | Flavonoid at 12 weeks | Placebo pre-study | Placebo at 12 weeks |
|---|---|---|---|---|
| Constipation | 1.8 | 2.2 | 1.7 | 1.9 |
| Heartburn | 1.8 | 2.9* | 1.7 | 1.8 |
| Bloating | 2.1 | 2.3 | 1.9 | 2.3 |
| Diarrhea | 1.7 | 2.0 | 1.2 | 2.0 |
| Energy | 6.1 | 6.3 | 5.8 | 6.1 |
| Fever | 1.0 | 1.0 | 1.1 | 1.0 |
| Cough | 1.6 | 1.3 | 1.7 | 1.7 |
| Stuffy nose | 2.4 | 1.8 | 2.1 | 2.1 |
| Headache | 2.6 | 2.3 | 2.5 | 2.7 |
| Joint pain | 2.6 | 2.8 | 2.5 | 2.4 |
| Back pain | 2.3 | 2.3 | 2.1 | 2.3 |
| Allergies | 3.5 | 2.1 | 3.7 | 2.7 |
| Stress | 4.9 | 5.1 | 4.9 | 4.7 |
| Focus | 7.0 | 6.5 | 7.6 | 7.2 |
| Well-being | 8.0 | 7.8 | 8.2 | 8.3 |
| Sleep | 6.8 | 6.8 | 7.2 | 7.3 |

Intensity of symptoms scaled from 1 to 12, with 1 being none and 12 being very high.
*$P < 0.05$ group difference in change, pre-study to 12-week.

In addition, the serum diagnostics chemistries showed no group differences at 12 weeks, except for the level of SGTP, indicating that liver, kidney, and overall metabolic health were not negatively affected by treatments (Table 7).

TABLE 7

Serum Diagnostic Chemistries

| Serum Diagnostic Chemistry Variable | Flavonoid Pre-Study | Flavonoid 12-wk | Placebo Pre-Study | Placebo 12-wk | P-Value |
|---|---|---|---|---|---|
| Sodium (mEq/L) | 139 | 139 | 139 | 139 | 0.177 |
| Blood Urea Nitrogen (mg/dL) | 13.7 | 13.0 | 14.0 | 13.1 | 0.814 |
| Creatinine (mg/dL) | 0.73 | 0.74 | 0.74 | 0.74 | 0.974 |
| Protein | 6.93 | 6.90 | 6.82 | 6.86 | 0.324 |
| Albumin (g/dL) | 4.11 | 4.13 | 4.11 | 4.13 | 0.352 |
| Bilirubin (mg/dL) | 0.51 | 0.52 | 0.53 | 0.56 | 0.513 |
| Alkaline Phosphatase (IU/L) | 69.5 | 69.3 | 72.4 | 71.0 | 0.545 |
| Alanine Aminotransferase (U/L) (SGPT) | 20.3 | 17.8 | 17.1 | 17.1 | 0.010 |
| Calcium (mg/dL) | 9.49 | 9.48 | 9.39 | 9.28 | 0.886 |

Figure 6:
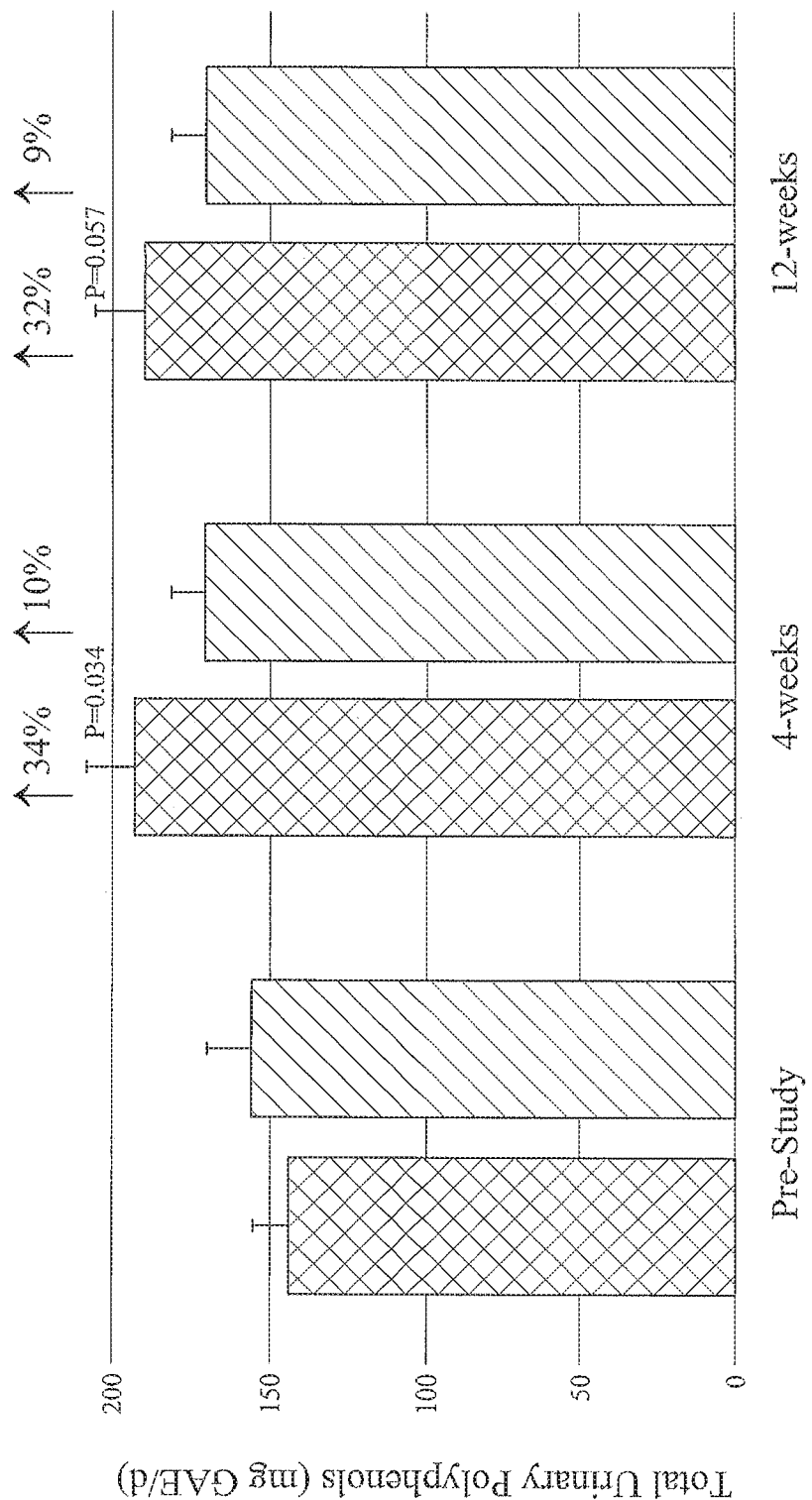
FIG. 6 graphically depicts the urinary phenolic concentration in the test group (left; administered a flavonoid composition) compared to the control group (right; administered placebo). Samples were obtained pre-study, at four weeks, and at 12 weeks.
Figure 7:
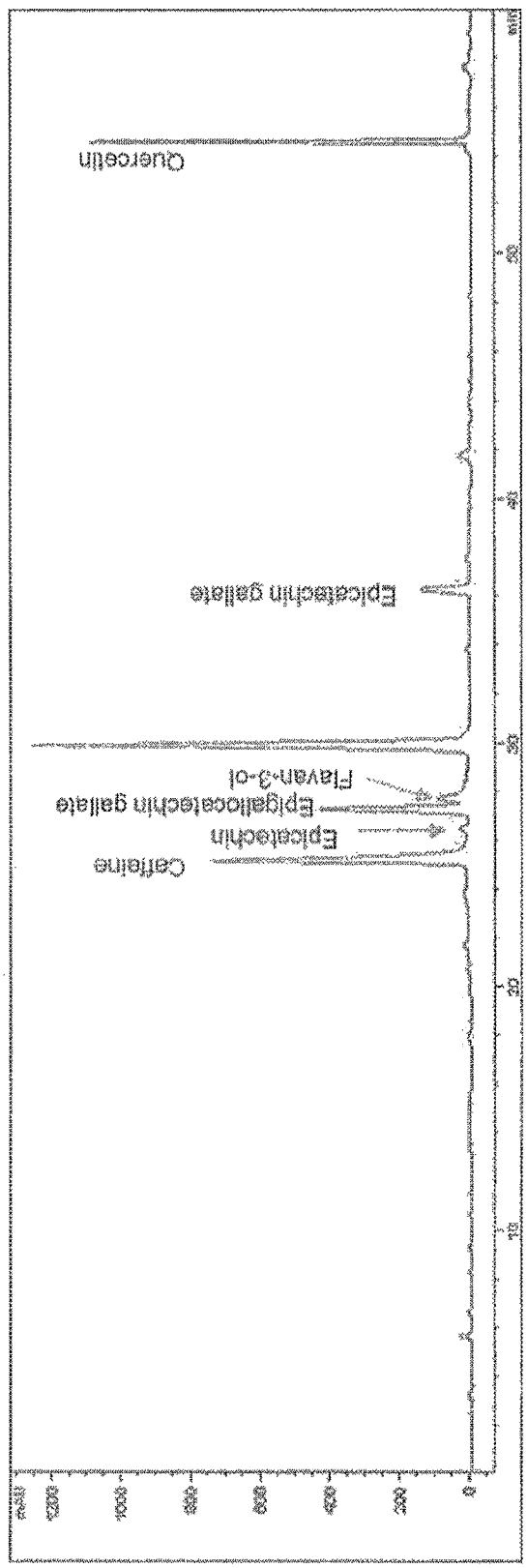
FIG. 7 depicts an exemplary chromatography profile of the flavonoids and caffeine in one embodiment of a flavonoid composition, recorded at 280 nm Compounds were quantified from standard curves created with reference compounds.

As depicted in FIGS. 5A-5D, subjects that were administered the flavonoid composition had elevated diet flavonoid intake, elevated diet EGCG, elevated diet anthocyanins, and elevated diet quercetin (flavonoid subjects depicted on the left, and control subjects on the right). Furthermore, as shown in FIG. 6, total urinary phenolics increased with subjects that were administered the flavonoid composition as compared to the control (flavonoid subjects depicted on the left, and control subjects on the right).

The flavonoid tablets were analyzed for phenolic content at weeks 4 and 12 of the study, and all ingredients were stable at pre-study values. The supplement increased total diet flavonoid intake by 181%, and provided a more diverse cocktail of flavonoids (anthocyanins, EGCG, quercetin) than typically ingested. This increase in dietary flavonoid intake translates to a significant decrease in mortality over time. Urine phenolic measurements showed a significant 23% increase in the flavonoid compared to placebo group during the 12-week study (interaction effect, P=0.041). This increase translates to a significant decrease in mortality over time. Flavonoid and placebo groups did not differ after the 12-week study in symptoms (except for small heartburn effect), or serum diagnostic chemistries, indicating that ingestion of the flavonoid composition vs. placebo is not related to adverse side-effects.

In summary, the flavonoid composition significantly increased total flavonoid, favan-3-ol, flavonol, and anthocyanidin intake to levels 44% above the U.S. mean for this age and sex group, despite starting with below average baselines. In fact, the increase in these compositions occurred even when lower amounts of flavonoids were provided than in previously conducted studies, indicating an increased bioavailability and bioactivity of the formulations provided herein.

Example 4

Influence of Ingesting a Flavonoid-Rich Supplement on the Human Metabolome and Concentration of Urine Phenolics The following example demonstrates the effects of ingesting a flavonoid-rich composition in overweight or obese subjects.

Subjects were provided placebo or flavonoid formulation tablets (in particular, the formulation described in Table 4) in overweight/obese women during a 12-week period. Individuals were invited to participate if they were non-smokers and free of heart disease, cancer, stroke, rheumatoid arthritis, and type I diabetes. The participants agreed to avoid non-steroidal anti-inflammatory drugs, dietary or herbal supplements that had the potential to influence inflammation or oxidative stress, and maintain normal diet and physical activity habits during the 12-week study. Subjects could not be pregnant or planning to be pregnant during the study, and not currently on a weight reducing plan or using weight loss medications. Participants recorded all food and beverage intake as part of a food record intake.

Figure 8:
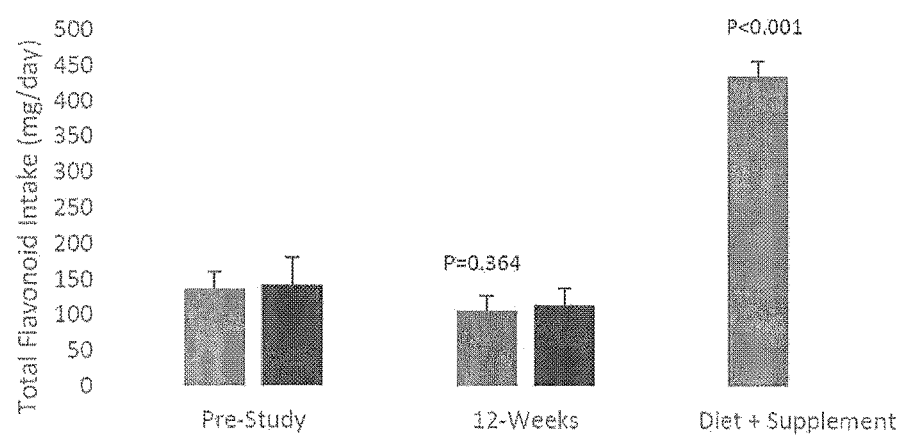
FIG. 8 graphically depicts the total flavonoid intake increase, from pre-study to 12-weeks. The bars on the left represent flavonoid supplementation, and the bars on the right represents placebo. Total flavonoid intake increased 217% as a result of taking the tablet (containing 329 mg of total flavonoid) compared to placebo. The p value over the flavonoid group bars represent the post-hoc analysis comparing the change from pre-study between groups.

Table 8 provides the results of pre-study and 12-week flavonoid intake, with the 12-week values including the flavonoid supplement. Table 8 shows significant increases in anthocyanins (335%), flavan-3-ols (142%), flavonols (1,107%), EGCG (534%), and quercetin (1,661%) in the flavonoid (with supplement) compared to placebo. FIG. 8 shows that the total flavonoid intake increased 217% in the flavonoid group as a result of taking the supplement compared to placebo.

TABLE 8

Food Record Flavonoid Intake

| | Flavonoid Pre-Study | Flavonoid 12-wk | Placebo Pre-Study | Placebo 12-wk | P-Value |
|---|---|---|---|---|---|
| Anthocyanins (mg) | 13.2 ± 4.9 | 57.4 ± 5.1 | 8.4 ± 2.5 | 17.6 ± 5.6 | <0.001 |
| Flavan-3-ols (mg) | 107 ± 20.8 | 259 ± 19.5 | 115 ± 35.2 | 85.0 ± 21.9 | <0.001 |
| EGCG | 15.7 ± 3.3 | 99.5 ± 3.1 | 17.3 ± 5.6 | 12.5 ± 3.5 | <0.001 |
| Flavonols (mg) | 9.36 ± 1.0 | 113 ± 0.9 | 9.09 ± 1.55 | 113 ± 0.9 | <0.001 |
| Quercetin (mg) | 6.19 ± 0.67 | 109 ± 0.5 | 5.55 ± 0.87 | 109 ± 0.5 | <0.001 |
| Flavanones (mg) | 7.46 ± 1.79 | 6.76 ± 1.76 | 10.9 ± 2.75 | 4.05 ± 1.15 | 0.077 |
| Isoflavones (mg) | 0.01 ± 0.01 | 0.19 ± 0.18 | 0.01 ± 0.01 | 0.02 ± 0.01 | 0.360 |
| Flavones (mg) | 0.47 ± 0.08 | 0.64 ± 0.08 | 0.42 ± 0.08 | 0.67 ± 0.14 | 0.500 |
| Vitamin C (mg) | 71.7 ± 10.4 | 175 ± 8.7 | 64.6 ± 7.4 | 64.6 ± 7.4 | <0.001 |
| Caffeine (mg) | 148 ± 29.8 | 247 ± 30.0 | 123 ± 13.5 | 125 ± 13.1 | 0.016 |

Figure 9:
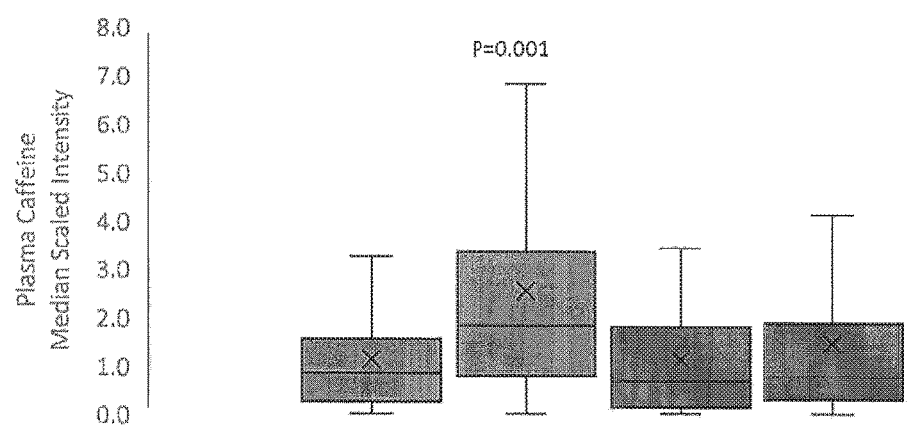
FIG. 9 graphically depicts the change in plasma caffeine levels after 12-weeks of supplementation with one embodiment of a flavonoid composition. Plasma caffeine levels are depicted from left to right as: flavonoid pre-study; flavonoid after 12 weeks; placebo pre-study; and placebo after 12 weeks.

In addition, serum samples were obtained to determine the serum diagnostic chemistries of subjects taking the flavonoid supplement compared to the placebo group. Specifically, serum levels of C-reactive protein (CRP), cytokine, oxidized LDL (oxLDL), and ferric reducing ability of plasma (FRAP) were determined. For CRP, high-sensitivity CRP was measured using an LX-20 clinical analyzer. For cytokine, the total plasma concentration of two cytokines was determined: monocyte chemoattractant protein-1 (MCP-1) and IL-6. The concentrations were determined using an electrochemiluminescence based solid-phase sandwich immunoassay. All samples and provided standards were analyzed in duplicate, and the intra-assay CV was 7.5% for the two cytokines measured. For oxLDL, the concentration was measuring using standard protocols for a competitive ELISA kit. FRAP was determined using a single electron transfer reaction, using water-soluble antioxidants in the plasma to reduce ferric iron to ferrous form, detectable at 593 nm. The results are shown in Table 9. FIG. 9 shows the change in plasma caffeine levels during 12 weeks of flavonoid or placebo supplementation.

TABLE 9

Serum Concentrations of CRP, Cytokine, oxLDL, and FRAP

|  | Flavonoid | | | Placebo | | | |
| --- | --- | --- | --- | --- | --- | --- | --- |
|  | Pre-Study | 4-wk | 12-wk | Pre-Study | 4-wk | 12-wk | P-Value |
| CRP (mg/L) | 4.66 ± 0.7 | 4.82 ± 0.7 | 4.64 ± 0.7 | 4.89 ± 0.76 | 5.19 ± 0.8 | 5.00 ± 0.8 | 0.750 |
| IL-6 (pg/mL) | 0.81 ± 0.1 | 0.88 ± 0.1 | 0.86 ± 0.1 | 0.96 ± 0.10 | 1.13 ± 0.1 | 0.95 ± 0.1 | 0.343 |
| MCP-1 (pg/mL) | 142 ± 5.7 | 129 ± 5.7 | 127 ± 4.9 | 141 ± 5.5 | 135 ± 6.0 | 129 ± 5.4 | 0.493 |
| oxLDL (U/mL/1000) | 55.0 ± 2.2 | 55.7 ± 2.3 | 55.1 ± 2.5 | 52.3 ± 2.3 | 52.2 ± 2.5 | 52.7 ± 2.2 | 0.969 |
| FRAP (μmol/L) | 495 ± 12.9 | 500 ± 11.7 | 513 ± 13.5 | 503 ± 12.2 | 492 ± 12.3 | 509 ± 15.2 | 0.243 |

In addition, the effects of the formulations on gut-derived phenolics were measured using a global metabolomics platform. Recovery standards were added prior to the first step in the extraction process for quality control purposes. To remove protein, dissociate small molecules bound to protein or trapped in the precipitated protein matrix, and to recover chemically diverse metabolites, proteins were precipitated with methanol under vigorous shaking for two minutes followed by centrifugation. Metabolites were identified by automated comparison of the ion features in the experimental samples to a reference library of chemical standard entries that included retention time, molecular weight, preferred adducts, and in-source fragments as well as associated MS spectra and curated by visual inspection for quality control. Identification of known chemical entities was based on comparison to metabolomics library entries of purified standards.

The metabolomics dataset included 729 compounds of known identity. Of these, 63 biochemicals exhibiting significant interaction effect (p<0.05) were identified, as listed in Table 10.

TABLE 10

Biochemicals identified by Metabolomics Dataset

| Biochemical Name | Super Pathway | p-value |
| --- | --- | --- |
| 2-aminobutyrate | Amino Acid | 0.0374 |
| 2-methylbutyrylcarnitine (C5) | Amino Acid | 0.0144 |
| 3-(3-hydroxyphenyl)propionate sulfate | Amino Acid | 0.0500 |
| alpha-ketobutyrate | Amino Acid | 0.0208 |
| guanidinosuccinate | Amino Acid | 0.0400 |
| homoarginine | Amino Acid | 0.0122 |
| hydantoin-5-propionic acid | Amino Acid | 0.0303 |
| N-acetylalanine | Amino Acid | 0.0005 |
| N-acetylaspartate (NAA) | Amino Acid | 0.0130 |
| N-acetylcarnosine | Amino Acid | 0.0438 |
| tiglylcarnitine (C5:1-DC) | Amino Acid | 0.0276 |
| vanillactate | Amino Acid | 0.0126 |
| bilirubin (Z,Z) | Cofactors and Vitamins | 0.0332 |
| gulonate* | Cofactors and Vitamins | 0.0316 |
| retinol (Vitamin A) | Cofactors and Vitamins | 0.0038 |
| 1-arachidonoyl-GPI (20:4)* | Lipid | 0.0474 |
| 1-palmitoyl-2-arachidonoyl-GPC (16:0/20:4n6) | Lipid | 0.0257 |
| 1-palmitoyl-2-arachidonoyl-GPI (16:0/20:4)* | Lipid | 0.0369 |
| 1-palmitoyl-2-oleoyl-GPC (16:0/18:1) | Lipid | 0.0434 |
| 1-palmitoyl-2-palmitoleoyl-GPC (16:0/16:1)* | Lipid | 0.0119 |
| 1-palmitoyl-GPI (16:0) | Lipid | 0.0014 |
| 1-stearoyl-2-linoleoyl-GPI (18:0/18:2) | Lipid | 0.0447 |
| 1-stearoyl-GPI (18:0) | Lipid | 0.0053 |
| 2-aminooctanoate | Lipid | 0.0158 |
| 2-hydroxyoctanoate | Lipid | 0.0108 |
| 2-hydroxystearate | Lipid | 0.0313 |
| 2-palmitoyl-GPC (16:0)* | Lipid | 0.0358 |
| 2-stearoyl-GPE (18:0)* | Lipid | 0.0059 |
| 3-hydroxybutyrylcarnitine (1) | Lipid | 0.0341 |
| 3-hydroxydecanoate | Lipid | 0.0468 |
| 3-hydroxyoctanoate | Lipid | 0.0080 |
| 3-hydroxysebacate | Lipid | 0.0183 |
| adipoylcarnitine (C6-DC) | Lipid | 0.0175 |
| dihomo-linolenate (20:3n3 or n6) | Lipid | 0.0430 |
| dihomo-linolenoyl-choline | Lipid | 0.0440 |
| glycosyl ceramide (d18:1/23:1, d17:1/24:1)* | Lipid | 0.0309 |
| glycosyl-N-stearoyl-sphingosine (d18:1/18:0) | Lipid | 0.0387 |
| pimeloylcarnitine/3-methyladipoylcarnitine (C7-DC) | Lipid | 0.0076 |
| pregn steroid monosulfate* | Lipid | 0.0346 |
| pregnen-diol disulfate* | Lipid | 0.0432 |
| sphingomyelin (d18:2/14:0, d18:1/14:1)* | Lipid | 0.0355 |
| sphingomyelin (d18:2/23:0, d18:1/23:1, d17:1/24:1)* | Lipid | 0.0360 |
| suberoylcarnitine (C8-DC) | Lipid | 0.0326 |
| taurocholenate sulfate | Lipid | 0.0467 |
| N1-methylinosine | Nucleotide | 0.0317 |
| N-acetylisoleucine | Nucleotide | 0.0107 |
| gamma-glutamylglycine | Peptide | 0.0429 |
| N-acetyl-beta-alanine | Peptide | 0.0042 |
| 1,2,3-benzenetriol sulfate (2) | Xenobiotics | 0.0300 |

TABLE 10-continued

Biochemicals identified by Metabolomics Dataset

| Biochemical Name | Super Pathway | p-value |
|---|---|---|
| 1,3,7-trimethylurate | Xenobiotics | 0.0037 |
| 1,3-dimethylurate | Xenobiotics | 0.0113 |
| 1,7-dimethylurate | Xenobiotics | 0.0109 |
| 1-methylurate | Xenobiotics | 0.0002 |
| 1-methylxanthine | Xenobiotics | 0.0051 |
| 3-methoxycatechol sulfate (1) | Xenobiotics | 0.0150 |
| 5-acetylamino-6-amino-3-methyluracil | Xenobiotics | 0.0160 |
| 5-acetylamino-6-formylamino-3-methyluracil | Xenobiotics | 0.0226 |
| benzoate | Xenobiotics | 0.0419 |
| caffeine | Xenobiotics | 0.0061 |
| ectoine | Xenobiotics | 0.0134 |
| erythritol | Xenobiotics | 0.0051 |
| eugenol sulfate | Xenobiotics | 0.0049 |
| paraxanthine | Xenobiotics | 0.0021 |

Figure 10A:
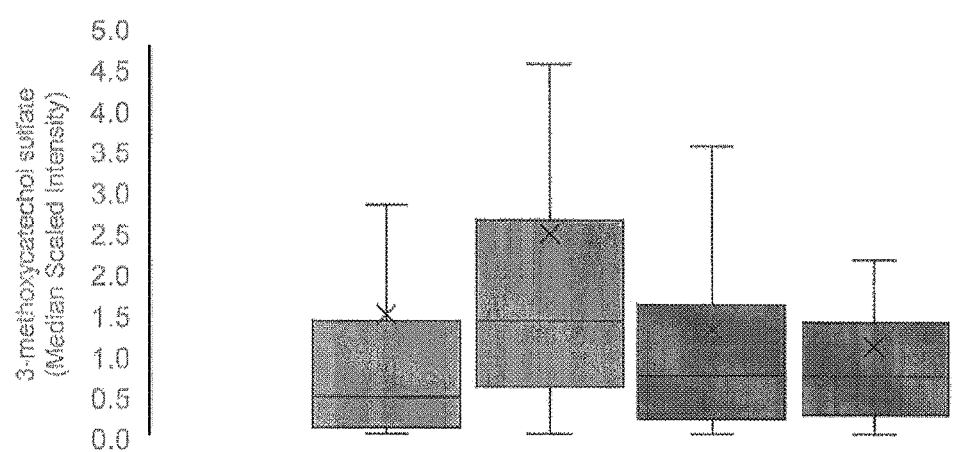
FIGS. 10A-10C graphically depict the increases in gut-derived phenolics in the subject having flavonoid supplementation compared to placebo.
Figure 10B:
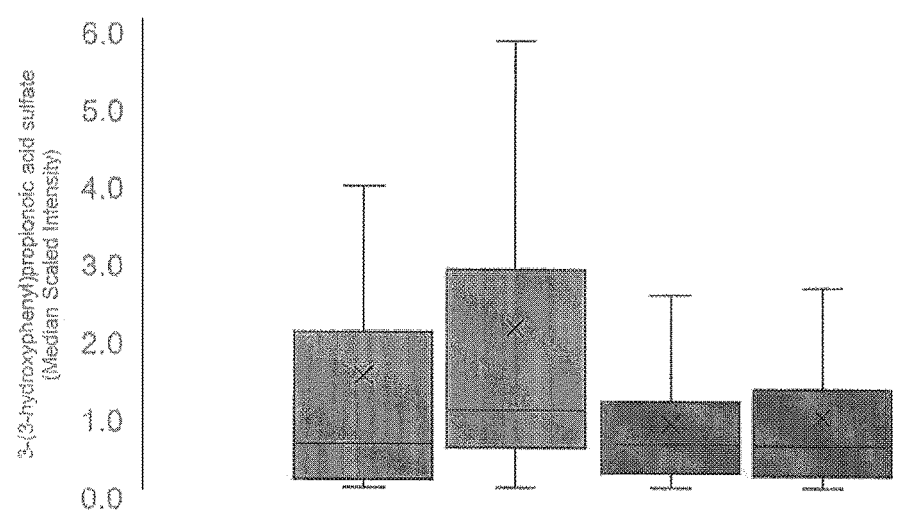
Figure 10C:
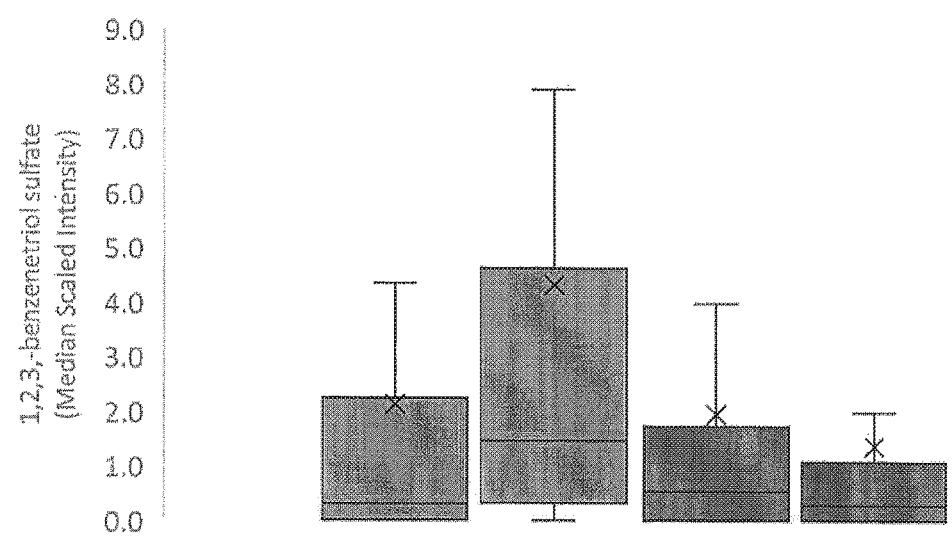

Of the 63 biochemicals listed in Table 10, 29 are lipids, 15 are xenobiotics, 14 are amino acids or peptides, 3 are cofactors and vitamins, and 2 are nucleotides. Of the 29 lipids, 15 are lysolipids, phospholipids, sphingolipids, or ceramides, 11 are fatty acids, 2 are steroids, and 1 is bile. Of the 15 xenobiotics, 9 are xanthines involved with caffeine metabolism, 2 are benzoates, 2 are food components, and 2 are chemicals. Of the 3 cofactors and vitamins, 1 is involved with vitamin A metabolism, 1 with ascorbate metabolism, and 1 with hemoglobin metabolism. At least three of the 63 biochemicals were gut-derived phenolics. At least three gut-derived phenolics increased in the flavonoid compared to placebo group, including 1,2,3-benzenetriol sulfate, 3-methoxycatechol sulfate, and 3-(3-hydroxyphenyl)propanoic acid sulfate. FIGS. 10A-10C show increases gut-derived phenolics in the flavonoid versus placebo group for three specific phenolics: 3-methoxycatechol sulfate (FIG. 10A; p=0.015); 3-(3-hydroxyphenol)propanoic acid sulfate (FIG. 10B; p=0.050); and 1,2,3-benzenetrial sulfate (FIG. 10C; p=0.030).

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided herein is intended merely to better illuminate the invention and does not pose a limitation on the scope of the invention otherwise claimed. No language in the specification should be construed as indicating any non-claimed element essential to the practice of the invention. Further, each of the references listed herein is hereby expressly incorporated by reference in its entirety.

It is contemplated that numerical values, as well as other values that are recited herein are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

Herein, the term "approximately" includes values ±10%. In preferred embodiments the term "approximately" includes values ±5%. In more preferred embodiments the term "approximately" includes values ±2%.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of increasing gut-derived phenolics in a subject, comprising:
administering a composition comprising bilberry fruit extract, green tea leaf extract, quercetin present in an amount of about 7.9% to about 16% (w/w), and omega 3 fatty acids to the subject.

2. The method of claim 1, wherein the increased gut-derived phenolics are one or more of 1,2,3-benzenetriol sulfate, 3-methoxycatechol sulfate, 3-(3-hydroxyphenyl)propanoic acid sulfate, 3-hydroxyhippurate, or 4-methylcatechol sulfate.

3. The method of claim 1, wherein the composition further comprises caffeine and vitamin C.

4. The method of claim 1, wherein the omega 3 fatty acids comprises docosahexaenoic acid and eicosapentaenoic acid.

5. The method of claim 1, wherein the composition further comprises a bioavailability enhancing agent selected from the group consisting of a solubilizing compound, a reducing compound, a stabilizing compound, a lubricating compound, an enteric coating, and a permeability enhancing compound.

6. The method of claim 1, wherein the bilberry extract is present in an amount of 10-500 mg, the green tea leaf extract is present in an amount of 10-500 mg, the quercetin is present in an amount of 10-500 mg, and the omega 3 fatty acids is present in an amount of 10-500 mg.

7. The method of claim 1, wherein the bilberry fruit extract comprises about 25% total anthocyanins.

8. The method of claim 1, wherein the green tea leaf extract comprises about 50% epigallocatechin 3-gallate (EGCG).

9. The method of claim 2, wherein the increased gut-derived phenolic 3-methoxycatechol sulfate is increased between 1-fold and 2 fold.

10. The method of claim 2, wherein the increased gut-derived phenolic 3-(3-hydroxyphenyl)propanoic acid sulfate is increased between 0.5-fold and 1 fold.

11. The method of claim 2, wherein the increased gut-derived 1,2,3-benzenetriol sulfate is increased between 1-fold and 2 fold.

12. The method of claim 1, wherein the composition is administered to a subject at a dose of two tablets twice daily.

13. The method of claim 1, wherein the composition is administered to a subject two to four times each day.

14. The method of claim 1, wherein the gut-derived phenolics are gut-derived phenolic metabolites.

15. The method of claim 3, wherein caffeine is present in an amount of 10-500 mg.

16. The method of claim 3, wherein the vitamin C is present in an amount of 10-500 mg.

17. The method of claim 1, wherein the composition further comprises one or more sugar, natural and artificial flavors, cellulose gum, sucralose, bamboo whole plant extract, guar gum, xanthan gum, citric acid, malic acid, or L-tartaric acid.

18. The method of claim 1, wherein the composition is formulated as a chewable tablet.

19. The method of claim 1, wherein the composition is administered to a subject prior to a meal.

* * * * *